United States Patent [19]
Daum et al.

[11] Patent Number: 5,625,074
[45] Date of Patent: Apr. 29, 1997

[54] SULPHONYLAMINOCARBONYLTRIAZO-LINONES

[75] Inventors: Werner Daum, Krefeld; Klaus-Helmut Müller, Düsseldorf; Michael Schwamborn, Köln; Peter Babczinski, Wuppertal; Hans-Joachim Santel, Leverkusen; Robert R. Schmidt, Bergisch Gladbach; Harry Strang, Düsseldorf, all of Germany

[73] Assignee: Bayer Aktiengesellschaft, Leverkusen, Germany

[21] Appl. No.: 632,984

[22] Filed: Apr. 16, 1996

Related U.S. Application Data

[62] Division of Ser. No. 356,933, Dec. 15, 1994, Pat. No. 5,532,378, which is a division of Ser. No. 31,426, Mar. 15, 1993, Pat. No. 5,405,970, which is a division of Ser. No. 816,365, Dec. 30, 1991, Pat. No. 5,241,074, which is a division of Ser. No. 692,439, Apr. 29, 1991, Pat. No. 5,094,683, which is a division of Ser. No. 556,052, Jul. 20, 1990, Pat. No. 5,057,144, which is a continuation-in-part of Ser. No. 337,775, Apr. 13, 1989, abandoned.

[30] Foreign Application Priority Data

| May 9, 1988 | [DE] | Germany | 38 15 765.9 |
| Oct. 12, 1989 | [DE] | Germany | 39 34 081.3 |

[51] Int. Cl.[6] .................. C07D 249/12; C07D 249/14
[52] U.S. Cl. .................. 548/263.8; 548/263.2; 548/263.4
[58] Field of Search .................. 548/263.2, 263.4, 548/263.8

[56] References Cited

U.S. PATENT DOCUMENTS

| 4,948,417 | 8/1990 | Lindig et al. | 548/263.2 |
| 5,166,356 | 11/1992 | Findeisen et al. | 548/263.8 |
| 5,241,074 | 8/1993 | Daum et al. | 548/263.8 |

*Primary Examiner*—Patricia L. Morris
*Attorney, Agent, or Firm*—Sprung Horn Kramer & Woods

[57] ABSTRACT

Herbicidal sulphonylaminocarbonyltriazolinones of the formula $$R^3-SO_2-NH-CO-N \overset{O}{\underset{N=\!\!\!=}{\diagup\!\!\!\diagdown}} \!\!\!\!\!\!\!\!\!\!\!\!\!\!\!\!\underset{R^2}{\overset{N-R^1}{}} \qquad (I)$$

in which $R^1$ represents hydrogen, hydroxyl or amino, or represents an optionally substituted radical from the series comprising alkyl, alkenyl, alkinyl, cycloalkyl, aralkyl, aryl, alkoxy, alkenyloxy, alkylamino and dialkylamino, $R^2$ represents hydrogen, hydroxyl, mercapto or amino, or represents an optionally substituted radical from the series comprising alkyl, cycloalkyl, cycloalkenyl, aralkyl, aryl, alkoxy, alkylamino and dialkylamino, and $R^3$ represents an optionally substituted radical from the series comprising alkyl, aralkyl, aryl and heteroaryl, and salts thereof. Intermediates of the formula $$HN \overset{O}{\underset{N=\!\!\!=}{\diagup\!\!\!\diagdown}} \!\!\!\!\!\!\!\!\!\!\!\!\!\!\!\!\underset{A^2}{\overset{N-A^1}{}} \qquad (IIa)$$

in which $A^1$ represents in each case optionally substituted alkyl, alkenyl, cycloalkyl, alkoxy or dialkylamino and $A^2$ represents hydrogen, or represents in each case optionally substituted alkyl, cycloalkyl, aralkyl, aryl or alkoxy, provided that both $A^1$ and $A^2$ do not simultaneously represent alkyl, are also new.

20 Claims, No Drawings

SULPHONYLAMINOCARBONYLTRIAZO-LINONES

This is a division of application Ser. No. 08/356,933, filed on Dec. 15, 1994, now U.S. Pat. No. 5,532,378, which is a division of application Ser. No. 08/031,426, filed on Mar. 15, 1993, now U.S. Pat. No. 5,405,970, which is a division of application Ser. No. 07/816,365, filed on Dec. 30, 1991, now U.S. Pat. No. 5,241,074, which is a division of application Ser. No. 07/692,439, filed on Apr. 29, 1991, now U.S. Pat. No. 5,094,683, which is a divsion of application Ser. No. 07/556,052, filed on Jul. 20, 1990, now U.S. Pat. No. 5,057,144, which is a continuation-in-part of application Ser. No. 07/337,775, filed on Apr. 13, 1989, now abandoned.

The invention relates to new sulphonylaminocarbonyltriazolinones, to several processes for their preparation, and to their use as herbicides.

It is known that certain substituted aminocarbonylimidazolinones, such as, for example, 1-isobutylaminocarbonyl-2-imidazolidinone (isocarbamide), have herbicidal properties (cf. R. Wegler, Chemie der Pflanzenschutz-und Schädlingsbekämpfungsmittel [Chemistry of Plant Protection Agents and Pesticides], Vol. 5, p. 219, Springer-Verlag, Berlin-Heidelberg-New York, 1977). However, the action of this compound is not satisfactory in all respects. The new sulphonylaminocarbonyl-triazolinones of the general formula (I)

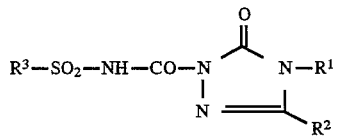
(I)

in which
R$^1$ represents hydrogen, hydroxyl or amino, or represents an optionally substituted radical from the series comprising alkyl, alkenyl, alkinyl, cycloalkyl, aralkyl, aryl, alkoxy, alkenyloxy, alkylamino and dialkylamino,
R$^2$ represents hydrogen, hydroxyl, mercapto or amino, or represents an optionally substituted radical from the series comprising alkyl, cycloalkyl, cycloalkenyl, aralkyl, aryl, alkoxy, alkylamino and dialkylamino, and
R$^3$ represents an optionally substituted radical from the series comprising alkyl, aralkyl, aryl and heteroaryl, as well as salts of compounds of the formula (I), have now been found.

The new sulphonylaminocarbonyltriazolinones of the general formula (I) are obtained when
a) triazolinones of the general formula (II)

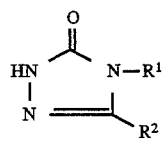
(II)

in which
R$^1$ and R$^2$ have the abovementioned meanings, are reacted with sulphonyl isocyanates of the general formula (III)

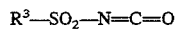
(III)

in which
R$^3$ has the abovementioned meaning, if appropriate in the presence of a diluent, or when b) triazolinone derivatives of the general formula (IV)

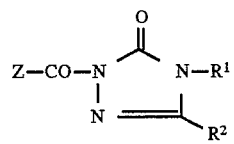
(IV)

in which
R$^1$ and R$^2$ have the abovementioned meanings and z represents halogen, alkoxy, aralkoxy or aryloxy, are reacted with sulphonamides of the general formula (V)

(V)

in which
R$^3$ has the abovementioned meaning, if appropriate in the presence of an acid acceptor and if appropriate in the presence of a diluent, or when
c) triazolinones of the general formula (II)

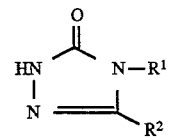
(II)

in which
R$^1$ and R$^2$ have the abovementioned meanings are reacted with sulphonamide derivatives of the general formula (VI)

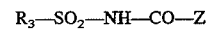
(VI)

in which
R$^3$ has the abovementioned meaning and
Z represents halogen, alkoxy, aralkoxy or aryloxy, if appropriate in the presence of an acid acceptor and if appropriate in the presence of a diluent, and, if appropriate, salts are formed by customary methods from the compounds of the formula (I) prepared by process (a), (b) or (c).

The new sulphonylaminocarbonyltriazolinones of the general formula (I) and their salts are distinguished by a powerful herbicidal activity. Surprisingly, the new compounds of the formula (I) show a considerably better herbicidal action than the known herbicide 1-isobutyl-aminocarbonyl-2-imidazolidinone (isocarbamide), which has a similar structure.

The invention preferably relates to compounds of the formula (I) in which
R$^1$ represents hydrogen, hydroxyl or amino, or represents C$_1$–C$_6$-alkyl which is optionally substituted by fluorine, chlorine, bromine, cyano, C$_1$–C$_4$-alkoxy, C$_1$–C$_4$-alkylcarbonyl or C$_1$–C$_4$-alkoxy-carbonyl, or represents C$_3$–C$_6$-alkenyl or C$_3$–C$_6$-alkinyl, each of which is optionally substituted by fluorine, chlorine and/or bromine, or represents C$_3$–C$_6$-cycloalkyl which is optionally substituted by fluorine, chlorine, bromine and/or C$_1$–C$_4$-alkyl, or represents phenyl-C$_1$–C$_3$-alkyl which is optionally substituted by fluorine, chlorine, bromine, cyano, nitro, C$_1$–C$_4$-alkyl, trifluoromethyl, C$_1$–C$_4$-alkoxy and/or C$_1$–C$_4$-alkoxy-carbonyl, or represents phenyl which is optionally substituted by fluorine, chlorine, bromine, cyano, nitro, C$_1$–C$_4$-alkyl, trifluoromethyl, C$_1$–C$_4$-alkoxy, fluorine- and/or chlorine-substituted C$_1$–C$_3$-alkoxy, C$_1$–C$_4$-alkylthio, fluorine- and/or chlorine-substituted C$_1$–C$_3$-alkylthio, C$_1$–C$_4$-alkylsulphinyl, C$_1$–C$_4$-alkylsulphonyl and/or C$_1$–C$_4$-alkoxy-carbonyl, or represents C$_1$–C$_6$-alkoxy which is optionally substituted by fluorine, chlorine, cyano, phenyl, $C_1-C_4$-alkoxy or $C_1-C_4$-alkoxycarbonyl, or represents $C_3-C_4$-alkenyloxy, or represents $C_1-C_4$-alkylamino which is optionally substituted by fluorine, cyano, $C_1-C_4$-alkoxy or $C_1-C_4$-alkoxycarbonyl, or represents di-$(C_1-C_4$-alkyl)-amino, $R^2$ represents hydrogen, hydroxyl, mercapto or amino, or represents $C_1-C_6$-alkyl which is optionally substituted by fluorine, chlorine, bromine, cyano, $C_3-C_6$-cycloalkyl, $C_1-C_4$-alkoxy or $C_1-C_4$-alkoxy-carbonyl, or represents $C_3-C_6$-cycloalkyl which is optionally substituted by fluorine, chlorine, bromine and/or $C_1-C_4$-alkyl, or represents cyclohexenyl, or represents phenyl-$C_1-C_3$-alkyl which is optionally substituted by fluorine, chlorine, bromine, cyano, nitro, $C_1-C_4$-alkyl, trifluoromethyl, $C_1-C_4$-alkoxy and/or $C_1-C_4$-alkoxycarbonyl, or represents phenyl which is optionally substituted by fluorine, chlorine, bromine, cyano, nitro, $C_1-C_4$-alkyl, trifluoromethyl, $C_1-C_4$-alkoxy, fluorine-and/or chlorine-substituted $C_1-C_3$-alkoxy, $C_1-C_4$-alkylthio, fluorine- and/or chlorine-substituted $C_1-C_3$-alkylthio, $C_1-C_4$-alkylsulphinyl, $C_1-C_4$-alkylsulphonyl and/or $C_1-C_4$-alkoxy-carbonyl, or represents $C_1-C_6$-alkoxy which is optionally substituted by fluorine, chlorine, cyano, $C_1-C_4$-alkoxy or $C_1-C_4$-alkoxy-carbonyl, or represents $C_1-C_4$-alkylamino or di-$(C_1-C_4$-alkyl)-amino, and $R^3$ represents the group

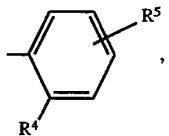

where
$R^4$ and $R^5$ are identical or different and represent hydrogen, fluorine, chlorine, bromine, iodine, nitro, $C_1-C_6$-alkyl (which is optionally substituted by fluorine, chlorine, bromine, cyano, carboxyl, $C_1-C_4$-alkoxycarbonyl, $C_1-C_4$-alkylamino-carbonyl, di-$(C_1-C_4$-alkyl)amino-carbonyl, hydroxyl, $C_1-C_4$-alkoxy, formyloxy, $C_1-C_4$-alkyl-carbonyloxy, $C_1-C_4$-alkoxycarbonyloxy, $C_1-C_4$-alkylaminocarbonyloxy, $C_1-C_4$-alkylthio, $C_1-C_4$-alkylsulphinyl, $C_1-C_4$-alkylsulphonyl, di-$(C_1-C_4$-alkyl)-aminosulphonyl, $C_3-C_6$-cycloalkyl or phenyl), or represent $C_2-C_6$-alkenyl (which is optionally substituted by fluorine, chlorine, bromine, cyano, $C_1-C_4$-alkoxy-carbonyl, carboxyl or phenyl), or represent $C_2-C_6$-alkinyl (which is optionally substituted by fluorine, chlorine, bromine, cyano, $C_1-C_4$-alkoxy-carbonyl, carboxyl or phenyl), or represent $C_1-C_4$-alkoxy (which is optionally substituted by fluorine, chlorine, bromine, cyano, carboxyl, $C_1-C_6$-alkoxy-carbonyl, $C_1-C_4$-alkoxy, $C_1-C_4$-alkylthio, $C_1-C_4$-alkylsulphinyl or $C_1-C_4$-alkylsulphonyl), or represent $C_1-C_4$-alkylthio (which is optionally substituted by fluorine, chlorine, bromine, cyano, carboxyl, $C_1-C_4$-alkoxy-carbonyl, $C_1-C_4$-alkylthio, $C_1-C_4$-alkylsulphinyl or $C_1-C_4$-alkylsulphonyl), or represent $C_3-C_6$-alkenyloxy (which is optionally substituted by fluorine, chlorine, bromine, cyano or $C_1-C_4$-alkoxy-carbonyl), or represent $C_2-C_6$-alkenylthio (which is optionally substituted by fluorine, chlorine, bromine, cyano, nitro, $C_1-C_3$-alkythio or $C_1-C_4$-alkoxycarbonyl), $C_3-C_6$-alkinyloxy, $C_3-C_6$-alkinylthio, or represent the radical —$S(O)_p$—$R^6$ where p represents the numbers 1 or 2 and $R^6$ represents $C_1-C_4$-alkyl (which is optionally substituted by fluorine, chlorine, bromine, cyano or $C_1-C_4$-alkoxy-carbonyl), $C_3-C_6$-alkenyl, $C_3-C_6$-alkinyl, $C_1-C_4$-alkoxy, $C_1-C_4$-alkoxy-$C_1-C_4$-alkylamino, $C_1-C_4$-alkylamino, di-$(C_1-C_4$-alkyl)-amino or phenyl, or represents the radical —NHOR$^7$ where $R^7$ represents $C_1-C_{12}$-alkyl (which is optionally substituted by fluorine, chlorine, cyano, $C_1-C_4$-alkoxy, $C_1-C_4$-alkylthio, $C_1-C_4$-alkylsulphinyl, $C_1-C_4$-alkylsulphonyl, $C_1-C_4$-alkylcarbonyl, $C_1-C_4$-alkoxycarbonyl, $C_1-C_4$-alkyl-aminocarbonyl or di-$(C_1-C_4$-alkyl)-amino-carbonyl), or represents $C_3-C_6$-alkenyl (which is optionally substituted by fluorine, chlorine or bromine), $C_3-C_6$-alkinyl, $C_3-C_6$-cycloalkyl, $C_3-C_6$-cycloalkyl-$C_1-C_2$-alkyl, phenyl-$C_1-C_2$-alkyl (which is optionally substituted by fluorine, chlorine, nitro, cyano, $C_1-C_4$-alkyl, $C_1-C_4$-alkoxy or $C_1-C_4$-alkoxy-carbonyl), or represents benzohydryl, or represents phenyl (which is optionally substituted by fluorine, chlorine, nitro, cyano, $C_1-C_4$-alkyl, trifluoromethyl, $C_1-C_4$-alkoxy, $C_1-C_2$-fluoroalkoxy, $C_1-C_4$-alkylthio, trifluoromethylthio or $C_1-C_4$-alkoxycarbonyl), $R^4$ and/or $R^5$ furthermore represent phenyl or phenoxy, or represent $C_1-C_4$-alkylcarbonylamino, $C_1-C_4$-alkoxycarbonylamino, $C_1-C_4$-alkylaminocarbonylamino, di-$(C_1-C_4$-alkyl) aminocarbonylamino, or represent the radical —CO—$R^8$, where $R^8$ represents $C_1-C_6$-alkyl, $C_1-C_6$-alkoxy, $C_3-C_6$-cycloalkoxy, $C_3-C_6$-alkenyloxy, $C_1-C_4$-alkylthio, $C_1-C_4$-alkylamino, $C_1-C_4$-alkoxyamino, $C_1-C_4$-alkoxy-$C_1-C_4$-alkyl-amino or di-$(C_1-C_4$-alkyl)-amino (each of which is optionally substituted by fluorine and/or chlorine), $R^4$ and/or $R^5$ furthermore represent trimethylsilyl, thiazolinyl, $C_1-C_4$-alkylsulphonyloxy, di-$(C_1-C_4$-alkyl)-aminosulphonylamino, or represent the radical —CH=N—$R^9$, where $R^9$ represents $C_1-C_6$-alkyl which is optionally substituted by fluorine, chlorine, cyano, carboxyl, $C_1-C_4$-alkoxy, $C_1-C_4$-alkylthio, $C_1-C_4$-alkylsulphinyl or $C_1-C_4$-alkylsulphonyl, or represents benzyl which is optionally substituted by fluorine or chlorine, or represents $C_3-C_6$-alkenyl or $C_3-C_6$-alkinyl, each of which is optionally substituted by fluorine or chlorine, or represents phenyl which is optionally substituted by fluorine, chlorine, bromine, $C_1-C_4$-alkyl, $C_1-C_4$-alkoxy, trifluoromethyl, trifluoromethoxy or trifluoromethylthio, or represents $C_1-C_6$-alkoxy, $C_3-C_6$-alkenoxy, $C_3-C_6$-alkinoxy or benzyloxy, each of which is optionally substituted by fluorine and/or chlorine, or represents amino, $C_1-C_4$-alkylamino, di-$(C_1-C_4$-alkyl)-amino, phenylamino, $C_1-C_4$-alkyl-carbonyl-amino, $C_1-C_4$-alkoxy-carbonylamino or $C_1-C_4$-alkylsulphonylamino, or represents phenylsulphonylamino which is optionally substituted by fluorine, chlorine, bromine or methyl, furthermore $R^3$ represents the radical

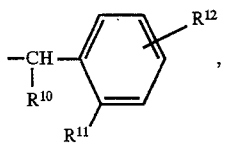

where $R^{10}$ represents hydrogen or $C_1-C_4$-alkyl, $R^{11}$ and $R^{12}$ are identical or different and represent hydrogen, fluorine, chlorine, bromine, nitro, cyano, $C_1-C_4$-alkyl (which is optionally substituted by fluorine and/or chlorine), $C_1-C_4$-alkoxy (which is optionally substituted by fluorine and/or chlorine), carboxyl, $C_1-C_4$-alkoxy-carbonyl, dimethylaminocarbonyl, $C_1-C_4$-alkylsulphonyl or di-($C_1-C_4$-alkyl)-aminosulphonyl;

furthermore $R^3$ represents the radical

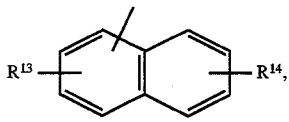

where $R^{13}$ and $R^{14}$ are identical or different and represent hydrogen, fluorine, chlorine, bromine, nitro, cyano, $C_1-C_4$-alkyl (which is optionally substituted by fluorine and/or chlorine) or $C_1-C_4$-alkoxy (which is optionally substituted by fluorine and/or chlorine);

furthermore $R^3$ represents the radical

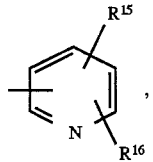

where $R^{15}$ and $R^{16}$ are identical or different and represent hydrogen, fluorine, chlorine, bromine, nitro, cyano, $C_1-C_4$-alkyl (which is optionally substituted by fluorine and/or chlorine), $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (each of which is optionally substituted by fluorine and/or chlorine), or represent di-($C_1-C_4$-alkyl)-aminosulphonyl or $C_1-C_4$-alkoxy-carbonyl or dimethylaminocarbonyl;

furthermore $R^3$ represents the radical

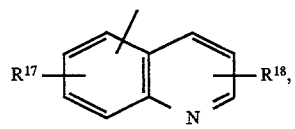

where $R^{17}$ and $R^{18}$ are identical or different and represent hydrogen, fluorine, chlorine, bromine, $C_1-C_4$-alkyl (which is optionally substituted by fluorine and/or bromine), $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (each of which is optionally substituted by fluorine and/or chlorine), or represent di-($C_1-C_4$-alkyl -aminosulphonyl;

furthermore $R^3$ represents the radical

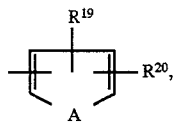

where $R^{19}$ and $R^{20}$ are identical or different and represent hydrogen, fluorine, chlorine, bromine, cyano, nitro, $C_1-C_4$-alkyl (which is optionally substituted by fluorine and/or chlorine), $C_1-C_4$-alkoxy (which is optionally substituted by fluorine and/or chlorine), $C_1-C_4$-alkylthio, $C_1-C_4$-alkylsulphinyl or $C_1-C_4$-alkylsulphonyl (which is optionally substituted by fluorine and/or chlorine), di-($C_1-C_4$-alkyl)-aminosulphonyl, $C_1-C_4$-alkoxy-carbonyl or dimethylaminocarbonyl, and A represents oxygen, sulphur or the group N—$Z^1$, where $Z^1$ represents hydrogen, $C_1-C_4$-alkyl (which is optionally substituted by fluorine, chlorine, bromine or cyano), $C_3-C_6$-cycloalkyl, benzyl, phenyl (which is optionally substituted by fluorine, chlorine, bromine or nitro), $C_1-C_4$-alkylcarbonyl, $C_1-C_4$-alkoxy-carbonyl or di-($C_1-C_4$-alkyl)-aminocarbonyl;

furthermore $R^3$ represents the radical

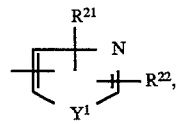

where $R^{21}$ and $R^{22}$ are identical or different and represent hydrogen, $C_1-C_4$-alkyl, halogen, $C_1-C_4$-alkoxycarbonyl, $C_1-C_4$-alkoxy or $C_1-C_4$-halogenoalkoxy, $Y^1$ represents sulphur or the group N—$R^{23}$, where $R^{23}$ represents hydrogen or $C_1-C_4$-alkyl;

furthermore $R^3$ represents the radical

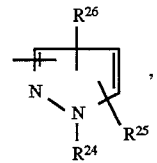

where $R^{24}$ represents hydrogen, $C_1-C_4$-alkyl, benzyl, quinolinyl or phenyl, $R^{25}$ represents hydrogen, halogen, cyano, nitro, $C_1-C_4$-alkyl (which is optionally substituted by fluorine and/or chlorine), $C_1-C_4$-alkoxy (which is optionally substituted by fluorine and/or chlorine), dioxolanyl or $C_1$–$C_4$-alkoxy-carbonyl, and $R^{26}$ represents hydrogen, halogen or $C_1$–$C_4$-alkyl;

furthermore $R^3$ represents one of the groups listed below,

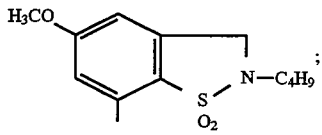

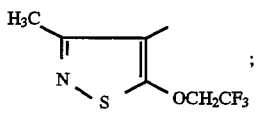

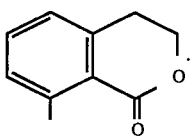

The invention furthermore preferably relates to the sodium, potassium, magnesium, calcium, ammonium, $C_1$–$C_4$-alkylammonium, di-($C_1$–$C_4$-alkyl)-ammonium, tri-($C_1$–$C_4$-alkyl)-ammonium, $C_5$- or $C_6$-cycloalkyl-ammonium and di-($C_1$–$C_2$-alkyl)-benzyl-ammonium salts of compounds of the formula (I) in which $R^1$, $R^2$ and $R^3$ have the meanings mentioned above as being preferred.

In particular, the invention relates to compounds of the formula (I) in which $R^1$ represents hydrogen, or represents $C_1$–$C_4$-alkyl which is optionally substituted by fluorine, chlorine, bromine, cyano, methoxy or ethoxy, or represents allyl, or represents $C_3$–$C_6$-cycloalkyl, or represents phenyl, or represents benzyl, or represents $C_1$–$C_3$-alkoxy, or represents $C_1$–$C_3$-alkylamino, or represents di-($C_1$–$C_2$-alkyl)-amino, $R^2$ represents hydrogen, or represents $C_1$–$C_4$-alkyl which is optionally substituted by fluorine and/or chlorine or by methoxy or ethoxy, or represents $C_3$–$C_6$-cycloalkyl, or represents phenyl, or represents $C_1$–$C_3$-alkoxy, or represents $C_1$–$C_3$-alkylamino, or represents di-($C_1$–$C_2$-alkyl)-amino, and $R^3$ represents the group

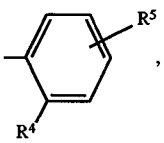

where $R^4$ represents fluorine, chlorine, bromine, methyl, trifluoromethyl, methoxy, difluoromethoxy, trifluoromethoxy, 2-chloro-ethoxy, 2-methoxyethoxy, $C_1$–$C_3$-alkylthio, $C_1$–$C_3$-alkylsulphinyl, $C_1$–$C_3$-alkylsulphonyl, dimethylaminosulphonyl, diethylaminosulphonyl, N-methoxy-N-methylamino-sulphonyl, phenyl, phenoxy or $C_1$–$C_3$-alkoxy-carbonyl, and $R^5$ represents hydrogen, fluorine, chlorine or bromine;

furthermore $R^3$ represents the radical

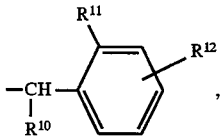

where $R^{10}$ represents hydrogen, $R^{11}$ represents fluorine, chlorine, bromine, methyl, methoxy, difluoromethoxy, trifluoromethoxy, ethoxy, methoxycarbonyl, ethoxycarbonyl, methylsulphonyl or dimethylaminosulphonyl, and $R^{12}$ represents hydrogen;

furthermore $R^3$ represents the radical

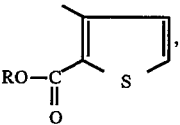

where R represents $C_1$–$C_4$-alkyl, or represents the radical

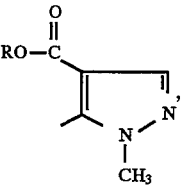

where R represents $C_1$–$C_4$-alkyl.

Examples of the compounds according to the invention are listed in Table 1 below—cf. also the Preparation Examples.

TABLE 1

Examples of the compounds of the formula (I)

$$R^3-SO_2-NH-CO-N(-CO-N(R^1)=C(R^2)-N=)$$  (I)

| $R^1$ | $R^2$ | $R^3$ |
|---|---|---|
| cyclopropyl | H | 2-F-phenyl |
| cyclopropyl | H | 2-Cl-phenyl |
| CH$_2$—CH=CH$_2$ | C$_2$H$_5$ | 2-OCF$_3$-benzyl |
| OCH$_3$ | C$_3$H$_7$ | 2-OCHF$_2$-benzyl |
| O—CH$_2$—CH=CH$_2$ | cyclopropyl | 3-methyl-2-(COOCH$_3$)-thiophene |
| C$_2$H$_5$ | C$_4$H$_4$-n | 2-COOC$_2$H$_5$-phenyl |
| CH$_3$ | C$_3$H$_7$ | 2-SO$_2$NHOCH$_3$-phenyl |
| cyclopentyl | C$_3$H$_7$ | 2-SO$_2$N(CH$_3$)$_2$-phenyl |
| CH$_3$ | C$_2$H$_5$ | 2,4-dichlorophenyl |

TABLE 1-continued

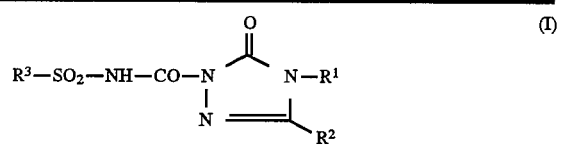

Examples of the compounds of the formula (I)

| R¹ | R² | R³ |
|---|---|---|
| C₂H₅ | C₃H₇ | 3-Br-2-CH₃-phenyl |
| OC₂H₅ | cyclopropyl | 2-(COOCH₂—CH₂—Cl)-phenyl |
| OC₃H₇ | CH₃ | 1-methyl-4-(COOCH₃)-5-methyl-pyrazol-3-yl |
| CH₃ | C₃H₇ | 3-methyl-2-(COOCH₃)-thien-yl |
| N(CH₃)₂ | CH₂-cyclopropyl | 2-(COOCH₃)-6-(CH₂—)-phenyl |
| NH—CH₃ | cyclopropyl | 2-(COOCH₃)-6-(CH₂—)-phenyl |
| CH₃ | C₃H₇ | 2-(COOC₂H₅)-5-(F₂CHO)-phenyl |
| cyclopropyl | OCH₃ | 2-(OCF₃)-phenyl |
| cyclobutyl | OC₂H₂ | 2-(OCHF₂)-phenyl |

TABLE 1-continued

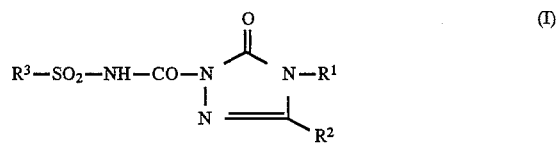

Examples of the compounds of the formula (I)

| R¹ | R² | R³ |
|---|---|---|
| CH₂—C₆H₅ | CH₂—C₆H₅ | 2-F-C₆H₄ |
| CH₂-cyclopropyl | C₃H₇ | 2-OCF₃-C₆H₄ |
| cyclopropyl | C₃H₇ | N-phenyl-pyrazole with COOCH₃ |
| CH₃ | C₂H₅ | methoxy-dimethyl benzisothiazole N—C₄H₉ |
| CH₃ | C₄H₉ | 2-methyl-3-CON(CH₃)₂-pyridine |
| cyclopropyl | C₃H₇ | 2-methyl-3-CON(CH₃)₂-pyridine |
| CH₃ | C₃H₇ | 2-biphenyl |
| C₂H₅ | C₂H₅ | 2-phenoxyphenyl |
| cyclopropyl | C₃H₇ | 2-(phenylsulfonyl)phenyl |

TABLE 1-continued
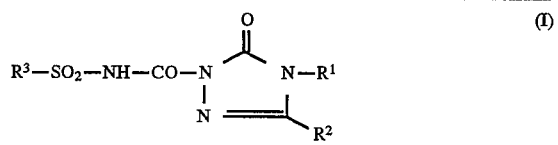
Examples of the compounds of the formula (I)

TABLE 1-continued $$R^3-SO_2-NH-CO-N\overset{O}{\underset{\underset{R^2}{\overset{\|}{N}}}{\|}}N-R^1 \qquad (I)$$

Examples of the compounds of the formula (I)

| R¹ | R² | R³ |
|---|---|---|
| CH₃ | cyclopropyl | pyrazole with COOC₂H₅, linked to isoquinoline |
| OCH₃ | C₂H₅ | pyrazole with COOC₂H₅, CH₃, linked to quinoline |
| OC₂H₅ | C₂H₅ | 4-Cl-2-CH₃-phenyl with COOCH(CH₃)₂ |
| CH₃ | CH₃ | 3-CF₃-2-CH₃-pyridyl |
| CH₃ | C₂H₅ | 4-Br-1-CH₃-5-CH₃-pyrazole |
| cyclopropyl | cyclopropyl | pyrazole with H₃COOC, CH₃, N-CH₃, Cl |
| CH₃ | CH₃ | 2,6-diCH₃-pyridyl-3-CON(CH₃)₂ |
| CH₃ | CH(CH₃)₂ | 2-OCF₃-benzyl (—CH₂—) |

TABLE 1-continued $$R^3-SO_2-NH-CO-N\overset{\overset{O}{\|}}{\underset{\underset{\|}{N}}{C}}N-R^1 \atop R^2 \qquad (I)$$

Examples of the compounds of the formula (I)

| R$^1$ | R$^2$ | R$^3$ |
|---|---|---|
| OCH$_2$—CH=CH$_2$ | C$_2$H$_5$ | 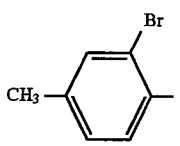 3-Br, 6-CH$_3$-phenyl |
| OCH$_3$ | C$_2$H$_5$ | 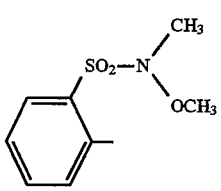 2-[SO$_2$—N(CH$_3$)(OCH$_3$)]-phenyl |
| CH$_3$ | CH(CH$_3$)$_2$ | 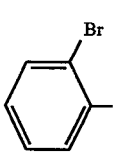 2-Br-phenyl |
| CH$_3$ | CH$_2$—CH=CH$_2$ | 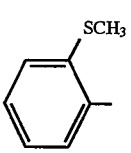 2-SCH$_3$-phenyl |
| CH$_3$ | CH$_2$—O—CH$_3$ | 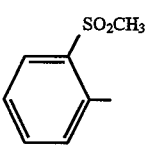 2-SO$_2$CH$_3$-phenyl |
| CH$_3$ | CH$_2$—O—C$_2$H$_5$ | 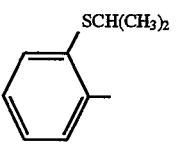 2-SCH(CH$_3$)$_2$-phenyl |
| C$_2$H$_5$ | C$_2$H$_4$—O—CH$_3$ | 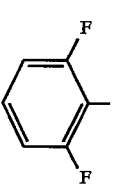 2,6-diF-phenyl |
| CH$_2$—CH=CH$_2$ | H | 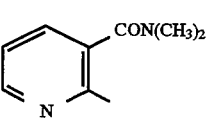 2-CH$_3$-3-CON(CH$_3$)$_2$-pyridyl |
| CH$_2$—CH=CH$_2$ | CH$_3$ | 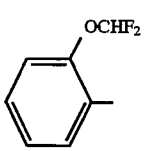 2-OCHF$_2$-phenyl |

TABLE 1-continued $$R^3-SO_2-NH-CO-N\underset{\underset{R^2}{\overset{\|}{N}}}{\overset{\overset{O}{\|}}{\diagup}}N-R^1 \quad (I)$$

Examples of the compounds of the formula (I)

| $R^1$ | $R^2$ | $R^3$ |
|---|---|---|
| $CH_2-CH=CH_2$ | $C_2H_5$ | 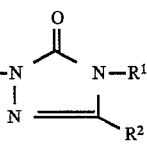 4-bromo-1-methylpyrazol-5-yl |
| $C_2H_5$ | cyclopropyl | 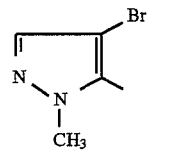 3-methyl-2-(methoxycarbonyl)thiophene |
| $CH_3$ | $C_3H_7$ | 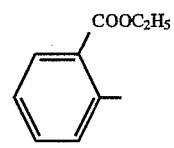 2-(ethoxycarbonyl)phenyl |
| $NH-CH_3$ | $C_2H_5$ | 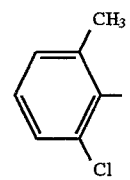 2,3-dimethyl-4-chlorophenyl |
| $NH-CH_3$ | cyclopropyl | 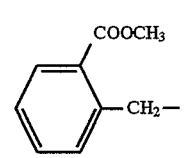 2-(methoxycarbonyl)benzyl |
| $CH_3$ | $C_3H_7$ | 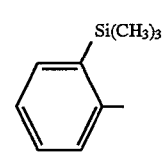 2-(trimethylsilyl)phenyl |
| cyclobutyl | $C_2H_5$ | 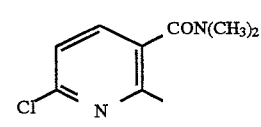 6-chloro-2-methyl-3-(N,N-dimethylcarbamoyl)pyridine |
| $C_2H_5$ | $C_4H_9$ | 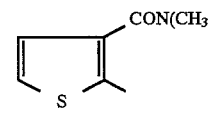 2-methyl-3-(N,N-dimethylcarbamoyl)thiophene |
| $CH_3$ | $C_3H_7$ | 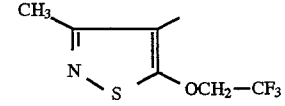 3,4-dimethyl-5-(2,2,2-trifluoroethoxy)isothiazole |

TABLE 1-continued
Examples of the compounds of the formula (I)
| R¹ | R² | R³ |
|---|---|---|
| △ (cyclopropyl) | $C_2H_5$ | 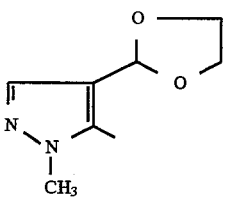 |
| $CH_3$ | △ |  |
| $C_2H_5$ | △ | 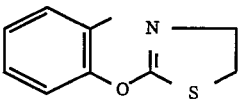 |
| $OCH_3$ | $CH(CH_3)_2$ |  |
| $OC_2H_5$ | $C_2H_5$ | 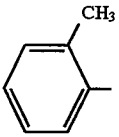 |
| $CH_3$ | H | 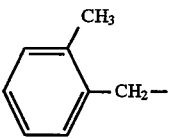 |
| $CH_3$ | $C_2H_5$ | 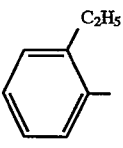 |
| $CH_3$ | $C_3H_7$ | 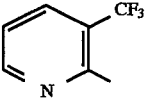 |
| $OCH_3$ | $C_3H_7$ | 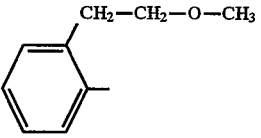 |

TABLE 1-continued $$R^3-SO_2-NH-CO-N \overset{\underset{N}{|}}{\underset{\parallel}{\phantom{N}}} \overset{O}{\underset{\parallel}{C}} N-R^1$$
$$\phantom{R^3-SO_2-NH-CO-N}N=\!\!=\!\!\underset{R^2}{C}$$

(I)

Examples of the compounds of the formula (I)

| R¹ | R² | R³ |
|---|---|---|
| OCH₃ | H | 2-(SO₂CH₃)-phenyl |
| CH₃ | C₂H₅ | 2-CH₃-3-Br-phenyl |
| CH₂—CH=CH₂ | CH₂—O—CH₃ | 2-OCHF₂-phenyl |
| CH₃ | C₂H₅ | 2-F-phenyl |
| CH₃ | C₃H₇ | 2-F-phenyl |
| CH₃ | CH(CH₃)₂ | 2-F-phenyl |
| CH₃ | C₄H₉ | 2-F-phenyl |
| CH₃ | CH₂CH(CH₃)₂ | 2-F-phenyl |
| CH₃ | C(CH₃)₃ | 2-F-phenyl |

TABLE 1-continued
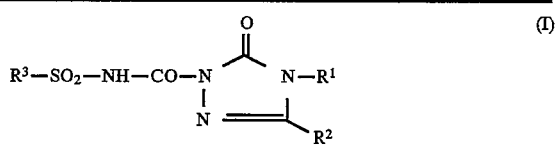 (I)
Examples of the compounds of the formula (I)
| R¹ | R² | R³ |
|---|---|---|
| CH₃ | C₂H₅ | 2-Cl-C₆H₄ |
| CH₃ | C₃H₇ | 2-Cl-C₆H₄ |
| CH₃ | CH(CH₃)₂ | 2-Cl-C₆H₄ |
| CH₃ | C₄H₉ | 2-Cl-C₆H₄ |
| CH₃ | CH₂CH(CH₃)₂ | 2-Cl-C₆H₄ |
| CH₃ | C(CH₃)₃ | 2-Cl-C₆H₄ |
| CH₃ | C₃H₇ | 2-Br-C₆H₄ |
| CH₃ | CH(CH₃)₂ | 2-Br-C₆H₄ |
| CH₃ | C₄H₉ | 2-Br-C₆H₄ |

TABLE 1-continued
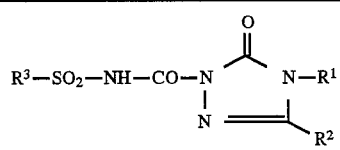
Examples of the compounds of the formula (I)
| R¹ | R² | R³ |
|---|---|---|
| CH₃ | CH₂CH(CH₃)₂ | 2-Br-C₆H₄ |
| CH₃ | C(CH₃)₃ | 2-Br-C₆H₄ |
| CH₃ | C₂H₅ | 2-CF₃-C₆H₄ |
| CH₃ | C₃H₇ | 2-CF₃-C₆H₄ |
| CH₃ | CH(CH₃)₂ | 2-CF₃-C₆H₄ |
| CH₃ | C₄H₉ | 2-CF₃-C₆H₄ |
| CH₃ | CH₂CH(CH₃)₂ | 2-CF₃-C₆H₄ |
| CH₃ | C(CH₃)₃ | 2-CF₃-C₆H₄ |
| CH₃ | C₂H₅ | 2-OCHF₂-C₆H₄ |

TABLE 1-continued $$R^3-SO_2-NH-CO-N\underset{N}{\overset{\overset{\displaystyle O}{\|}}{\underset{\|}{C}}}\underset{R^2}{\overset{N-R^1}{\diagup}} \qquad (I)$$

Examples of the compounds of the formula (I)

| R¹ | R² | R³ |
|---|---|---|
| CH₃ | C₃H₇ | 2-(OCHF₂)phenyl |
| CH₃ | CH(CH₃)₂ | 2-(OCHF₂)phenyl |
| CH₃ | C₄H₉ | 2-(OCHF₂)phenyl |
| CH₃ | CH₂CH(CH₃)₂ | 2-(OCHF₂)phenyl |
| CH₃ | C(CH₃)₃ | 2-(OCHF₂)phenyl |
| CH₃ | C₂H₅ | 2-(OCF₃)phenyl |
| CH₃ | C₃H₇ | 2-(OCF₃)phenyl |
| CH₃ | CH(CH₃)₂ | 2-(OCF₃)phenyl |
| CH₃ | C₄H₉ | 2-(OCF₃)phenyl |

TABLE 1-continued $$R^3-SO_2-NH-CO-N \begin{array}{c} O \\ \parallel \\ C \\ | \\ N \end{array} N-R^1$$
$$\phantom{R^3-SO_2-NH-CO-N}\begin{array}{c}|\\N\end{array}=\begin{array}{c}\\R^2\end{array}$$  (I)

Examples of the compounds of the formula (I)

| R¹ | R² | R³ |
|---|---|---|
| CH₃ | CH₂CH(CH₃)₂ | 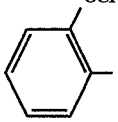 2-OCF₃-phenyl |
| CH₃ | C(CH₃)₃ | 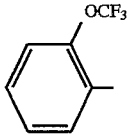 2-OCF₃-phenyl |
| C₂H₅ | CH₃ | 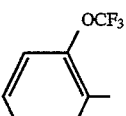 2-OCF₃-phenyl |
| C₃H₇ | CH₃ | 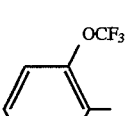 2-OCF₃-phenyl |
| CH₃ | C(CH₃)₃ | 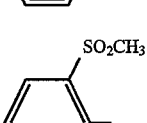 2-SO₂CH₃-phenyl |
| CH₃ | C₂H₅ | 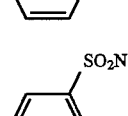 2-SO₂N(CH₃)₂-phenyl |
| CH₃ | C₃H₇ | 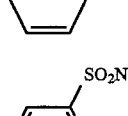 2-SO₂N(CH₃)₂-phenyl |
| CH₃ | CH(CH₃)₂ | 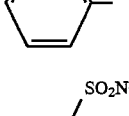 2-SO₂N(CH₃)₂-phenyl |
| CH₃ | C₄H₉ | 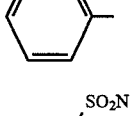 2-SO₂N(CH₃)₂-phenyl |

TABLE 1-continued
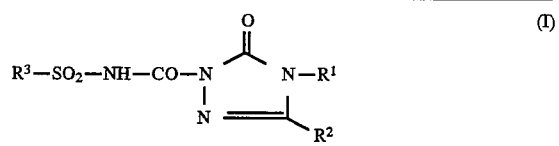
Examples of the compounds of the formula (I)
| R¹ | R² | R³ |
|---|---|---|
| CH₃ | CH₂CH(CH₃)₂ | 2-SO₂N(CH₃)₂-C₆H₄ |
| CH₃ | C(CH₃)₃ | 2-SO₂N(CH₃)₂-C₆H₄ |
| CH₃ | CH₃ | 2-COOCH₃-C₆H₄ |
| CH₃ | C₂H₅ | 2-COOCH₃-C₆H₄ |
| CH₃ | C₃H₇ | 2-COOCH₃-C₆H₄ |
| CH₃ | CH(CH₃)₂ | 2-COOCH₃-C₆H₄ |
| CH₃ | C₄H₉ | 2-COOCH₃-C₆H₄ |
| CH₃ | CH₂CH(CH₃)₂ | 2-COOCH₃-C₆H₄ |
| CH₃ | C(CH₃)₃ | 2-COOCH₃-C₆H₄ |

TABLE 1-continued
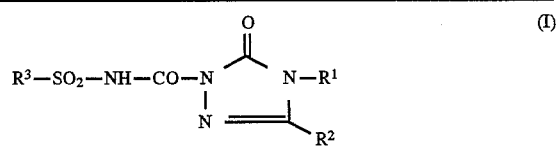
Examples of the compounds of the formula (I)
| $R^1$ | $R^2$ | $R^3$ |
|---|---|---|
| $C_2H_5$ | $CH_3$ | 2-($COOCH_3$)-C$_6$H$_4$ |
| $CH_3$ | $C_2H_5$ | 2-($COOC_2H_5$)-C$_6$H$_4$ |
| $CH_3$ | $C_3H_7$ | 2-($COOC_2H_5$)-C$_6$H$_4$ |
| $CH_3$ | $CH(CH_3)_2$ | 2-($COOC_2H_5$)-C$_6$H$_4$ |
| $CH_3$ | $C_4H_9$ | 2-($COOC_2H_5$)-C$_6$H$_4$ |
| $CH_3$ | $CH_2CH(CH_3)_2$ | 2-($COOC_2H_5$)-C$_6$H$_4$ |
| $CH_3$ | $C(CH_3)_3$ | 2-($COOC_2H_5$)-C$_6$H$_4$ |
| $CH_3$ | $C_2H_5$ | 2-($COOCH_3$)-C$_6$H$_4$-$CH_2$- |
| $CH_3$ | $C_3H_7$ | 2-($COOCH_3$)-C$_6$H$_4$-$CH_2$- |

TABLE 1-continued
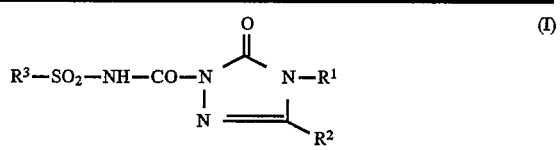
Examples of the compounds of the formula (I)
| R¹ | R² | R³ |
|---|---|---|
| CH₃ | CH(CH₃)₂ | 2-(COOCH₃)-C₆H₄-CH₂— |
| CH₃ | C₄H₉ | 2-(COOCH₃)-C₆H₄-CH₂— |
| CH₃ | CH₂CH(CH₃)₂ | 2-(COOCH₃)-C₆H₄-CH₂— |
| CH₃ | C(CH₃)₃ | 2-(COOCH₃)-C₆H₄-CH₂— |
| C₂H₅ | CH₃ | 2-(COOCH₃)-C₆H₄-CH₂— |
| C₃H₇ | CH₃ | 2-(COOCH₃)-C₆H₄-CH₂— |
| CH₃ | C₂H₅ | 2-(COOC₂H₅)-C₆H₄-CH₂— |
| CH₃ | C₃H₇ | 2-(COOC₂H₅)-C₆H₄-CH₂— |
| CH₃ | CH(CH₃)₂ | 2-(COOC₂H₅)-C₆H₄-CH₂— |

TABLE 1-continued $$R^3-SO_2-NH-CO-N\begin{array}{c}O\\\parallel\\C\\|\\N\end{array}N-R^1$$ (I)

Examples of the compounds of the formula (I)

| $R^1$ | $R^2$ | $R^3$ |
|---|---|---|
| CH$_3$ | C$_4$H$_9$ | 2-(COOC$_2$H$_5$)C$_6$H$_4$CH$_2$— |
| CH$_3$ | CH$_2$CH(CH$_3$)$_2$ | 2-(COOC$_2$H$_5$)C$_6$H$_4$CH$_2$— |
| CH$_3$ | C$_2$H$_5$ | 2-(OCHF$_2$)C$_6$H$_4$CH$_2$— |
| CH$_3$ | C$_3$H$_7$ | 2-(OCHF$_2$)C$_6$H$_4$CH$_2$— |
| CH$_3$ | CH(CH$_3$)$_2$ | 2-(OCHF$_2$)C$_6$H$_4$CH$_2$— |
| CH$_3$ | C$_4$H$_9$ | 2-(OCHF$_2$)C$_6$H$_4$CH$_2$— |
| CH$_3$ | CH$_2$CH(CH$_3$)$_2$ | 2-(OCHF$_2$)C$_6$H$_4$CH$_2$— |
| CH$_3$ | C(CH$_3$)$_3$ | 2-(OCHF$_2$)C$_6$H$_4$CH$_2$— |
| CH$_3$ | CH$_3$ | 3-methyl-2-(COOCH$_3$)thiophene |
| CH$_3$ | C$_2$H$_5$ | 3-methyl-2-(COOCH$_3$)thiophene |

TABLE 1-continued

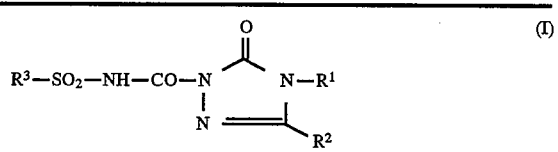

Examples of the compounds of the formula (I)

| R¹ | R² | R³ |
|---|---|---|
| CH₃ | C₃H₇ | 3-methyl-2-(methoxycarbonyl)thiophene |
| CH₃ | CH(CH₃)₂ | 3-methyl-2-(methoxycarbonyl)thiophene |
| CH₃ | C₄H₉ | 3-methyl-2-(methoxycarbonyl)thiophene |
| CH₃ | CH₂CH(CH₃)₂ | 3-methyl-2-(methoxycarbonyl)thiophene |
| CH₃ | CH₃ | 1,3-dimethyl-4-(methoxycarbonyl)pyrazole |
| CH₃ | C₂H₅ | 1,3-dimethyl-4-(methoxycarbonyl)pyrazole |
| CH₃ | C₃H₇ | 1,3-dimethyl-4-(methoxycarbonyl)pyrazole |
| CH₃ | CH(CH₃)₂ | 1,3-dimethyl-4-(methoxycarbonyl)pyrazole |
| CH₃ | C₄H₉ | 1,3-dimethyl-4-(methoxycarbonyl)pyrazole |
| CH₃ | CH₂CH(CH₃)₂ | 1,3-dimethyl-4-(methoxycarbonyl)pyrazole |

TABLE 1-continued $$R^3-SO_2-NH-CO-N\underset{N}{\overset{\overset{\displaystyle O}{\|}}{\underset{\|}{C}}}N-R^1$$
$$\phantom{R^3-SO_2-NH-CO-N}N=\!\!=\!\!\overset{\phantom{x}}{\underset{R^2}{C}}$$
(I)

Examples of the compounds of the formula (I)

| $R^1$ | $R^2$ | $R^3$ |
|---|---|---|
| $CH_3$ | $C(CH_3)_3$ | 1-methyl-5-methyl-4-COOCH$_3$-pyrazole |
| $CH_3$ | $C_2H_5$ | 1-methyl-5-methyl-4-COOC$_2$H$_5$-pyrazole |
| $CH_3$ | $C_3H_7$ | 1-methyl-5-methyl-4-COOC$_2$H$_5$-pyrazole |
| $CH_3$ | $CH(CH_3)_2$ | 1-methyl-5-methyl-4-COOC$_2$H$_5$-pyrazole |
| $CH_3$ | $C_4H_9$ | 1-methyl-5-methyl-4-COOC$_2$H$_5$-pyrazole |
| $CH_3$ | $CH_2CH(CH_3)_2$ | 1-methyl-5-methyl-4-COOC$_2$H$_5$-pyrazole |
| $CH_3$ | $C(CH_3)_3$ | 1-methyl-5-methyl-4-COOC$_2$H$_5$-pyrazole |
| $CH_3$ | $CH_3$ | 2-(OCF$_3$)-benzyl |
| $CH_3$ | $C_2H_5$ | 2-(OCF$_3$)-benzyl |

TABLE 1-continued
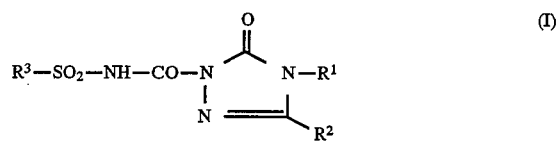
Examples of the compounds of the formula (I)
| R¹ | R² | R³ |
|---|---|---|
| CH₃ | C₃H₇ | 2-(OCF₃)C₆H₄-CH₂- |
| CH₃ | CH(CH₃)₂ | 2-(OCF₃)C₆H₄-CH₂- |
| CH₃ | C₄H₉ | 2-(OCF₃)C₆H₄-CH₂- |
| CH₃ | CH₂CH(CH₃)₂ | 2-(OCF₃)C₆H₄-CH₂- |
| CH₃ | C₂H₅ | 2,6-Cl₂C₆H₃- |
| CH₃ | C₃H₇ | 2,6-Cl₂C₆H₃- |
| CH₃ | CH(CH₃)₂ | 2,6-Cl₂C₆H₃- |
| CH₃ | C₄H₉ | 2,6-Cl₂C₆H₃- |

TABLE 1-continued $$R^3-SO_2-NH-CO-N\begin{array}{c}O\\\parallel\\C\end{array}N-R^1$$
$$\qquad\qquad\qquad\qquad\quad | \quad\;\;\;\|$$
$$\qquad\qquad\qquad\qquad\;\; N=C-R^2$$  (I)

Examples of the compounds of the formula (I)

| $R^1$ | $R^2$ | $R^3$ |
|---|---|---|
| $CH_3$ | $CH_2CH(CH_3)_2$ | 2,6-diCl-C$_6$H$_3$- |
| $CH_3$ | $C(CH_3)_3$ | 2,6-diCl-C$_6$H$_3$- |
| $CH_3$ | $C_2H_5$ | 2-SO$_2$CH$_3$-C$_6$H$_4$- |
| $CH_3$ | $C_3H_7$ | 2-SO$_2$CH$_3$-C$_6$H$_4$- |
| $CH_3$ | $C_3H_7$ | 2,6-diCl-C$_6$H$_3$-CH$_2$- |
| $CH_3$ | $CH(CH_3)_2$ | 2,6-diCl-C$_6$H$_3$-CH$_2$- |
| $CH_3$ | $C_4H_9$ | 2,6-diCl-C$_6$H$_3$-CH$_2$- |
| $CH_3$ | $CH_2CH(CH_3)_2$ | 2,6-diCl-C$_6$H$_3$-CH$_2$- |

TABLE 1-continued $$R^3-SO_2-NH-CO-N\overset{\overset{O}{\|}}{\underset{\underset{N}{|}}{C}}N-R^1 \quad\quad (I)$$
$$\underset{R^2}{\overset{\|}{N}}$$

Examples of the compounds of the formula (I)

| $R^1$ | $R^2$ | $R^3$ |
|---|---|---|
| $CH_3$ | $C(CH_3)_3$ | 2,6-dichlorobenzyl (–CH$_2$–C$_6$H$_3$Cl$_2$) |
| $CH_3$ | $CH(CH_3)_2$ | 2-(SO$_2$CH$_3$)-phenyl |
| $CH_3$ | $C_4H_9$ | 2-(SO$_2$CH$_3$)-phenyl |
| $CH_3$ | $CH_2CH(CH_3)_2$ | 2-(SO$_2$CH$_3$)-phenyl |
| $N(CH_3)_2$ | $N(CH_3)_2$ | 2-(OCH$_2$CH$_2$–Cl)-phenyl |

If, for example, 2,6-difluorophenyl isocyanate and 5-ethyl-4-methoxy-2,4-dihydro-3H-1,2,4-triazol-3-one are used as starting substances, the course of the reaction in process (a) according to the invention can be outlined by the following equation:

If, for example, 2-methylthio-benzenesulphonamide and 2-chlorocarbonyl-4-dimethylamino-2,4-dihydro-3H-1,2,4-triazol-3-one are used as starting substances, the course of the reaction in process (b) according to the invention can be outlined by the following equation:

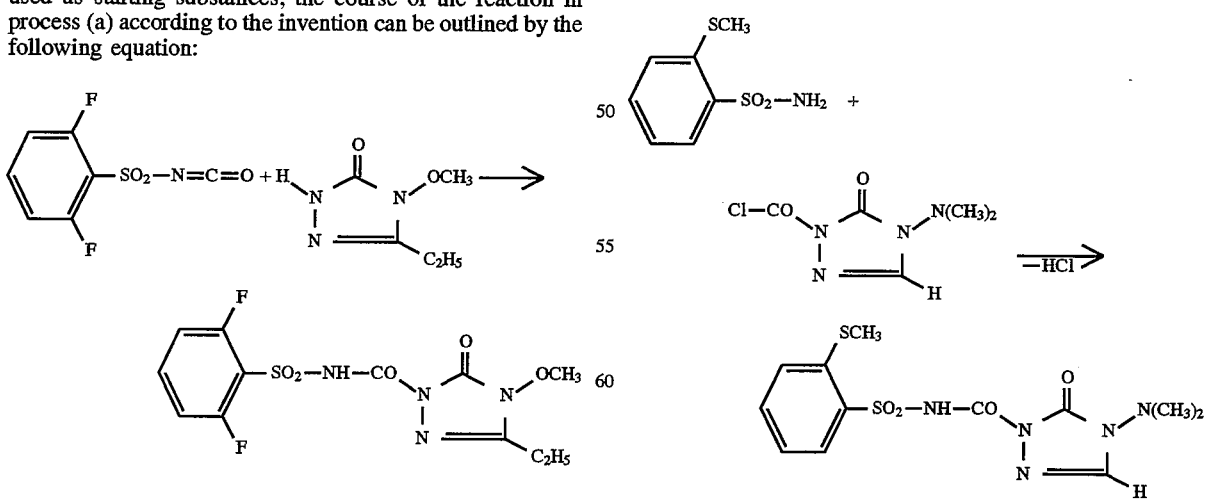

If, for example, N-methoxycarbonyl-2-methoxy-benzenesulphonamide and 5-diethylamino-4- difluoromethyl-2,4-dihydro-3H-1,2,4-triazol-3-one are used as starting substances, the course of the reaction in process (c) according to the invention can be outlined by the following equation:

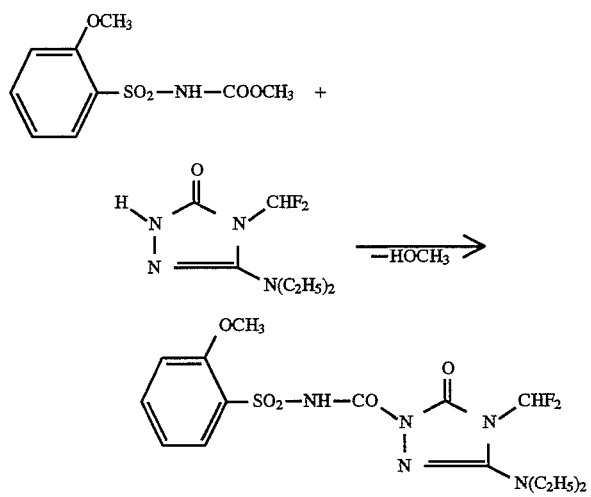

Formula (II) provides a general definition of the triazolinones to be used as starting substances in processes (a) and (c) according to the invention for the preparation of compounds of the formula (I).

In formula (II), $R^1$ and $R^2$ preferably, or in particular, have those meanings which have already been mentioned above in connection with the description of the compounds of the formula (I) according to the invention as being preferred, or particularly preferred, for $R^1$ and $R^2$.

Examples of the starting substances of the formula (II) are listed in Table 2 below.

TABLE 2

(II)

Examples of the starting substances of the formula (II)

| $R^1$ | $R^2$ |
|---|---|
| H | H |
| $CH_3$ | H |
| $C_2H_5$ | H |
| $C_3H_7$ | H |
| $CH(CH_3)_2$ | H |
| $C_4H_9$ | H |
| $CH_2CH(CH_3)_2$ | H |
| $C(CH_3)_3$ | H |
| H | $CH_3$ |
| H | $C_2H_5$ |
| H | $C_3H_7$ |
| H | $CH(CH_3)_2$ |
| H | $C_4H_9$ |
| H | $CH_2CH(CH_3)_2$ |
| H | $C(CH_3)_3$ |
| $CHF_2$ | H |
| $CH_2CH_2CN$ | H |
| $CH_2CH_2OCH_3$ | H |
| H | $CF_3$ |
| H | $CH_2OCH_3$ |
| H | $CH_2OC_2H_5$ |
| H | $CH_2CH_2OCH_3$ |

TABLE 2-continued (II)

Examples of the starting substances of the formula (II)

| $R^1$ | $R^2$ |
|---|---|
| $CH_3$ | $CH_3$ |
| $CH_3$ | $C_2H_5$ |
| $CH_3$ | $C_3H_7$ |
| $CH_3$ | $CH(CH_3)_2$ |
| $CH_3$ | $C_4H_9$ |
| $CH_3$ | $CH_2CH(CH_3)_2$ |
| $CH_3$ | $C(CH_3)_3$ |
| $C_2H_5$ | $CH_3$ |
| $C_3H_7$ | $CH_3$ |
| $CH(CH_3)_2$ | $CH_3$ |
| $C_4H_9$ | $CH_3$ |
| $CH_2CH(CH_3)_2$ | $CH_3$ |
| $C_2H_5$ | $C_2H_5$ |
| $C_3H_7$ | $C_3H_7$ |
| $CHF_2$ | $C_3H_7$ |
| $CHF_2$ | $CH_3$ |
| $CHF_2$ | $C_2H_5$ |
| $CH_3$ | $CF_3$ |
| $C_2H_5$ | $CF_3$ |
| $CF_2CHF_2$ | $CH_3$ |
| $C_2H_5$ | $C_3H_7$ |
| $C_2H_5$ | $C_4H_9$ |
| $C_6H_5$ | $CH_3$ |
| —CH(CH₂)(CH₂) (cyclopropyl) | $CH_3$ |
| $CH_3$ | —CH(CH₂)(CH₂) (cyclopropyl) |
| cyclobutyl | $CH_3$ |
| cyclopentyl | $CH_3$ |
| $CH_3$ | $N(CH_3)_2$ |
| $C_2H_5$ | $N(CH_3)_2$ |
| $C_2H_5$ | cyclopropyl |
| $C_3H_7$ | cyclopropyl |
| $OCH_3$ | cyclopropyl |
| cyclobutyl | $C_2H_5$ |
| cyclobutyl | $C_3H_7$ |
| cyclohexyl-H | $CH_3$ |

TABLE 2-continued $$\text{(II)} \quad \underset{N}{\overset{HN}{\vphantom{X}}}\!\!-\!\!\underset{\|}{\overset{O}{C}}\!\!-\!\!\underset{\|}{N}\!\!-\!\!R^1$$
with $=CR^2$ Examples of the starting substances of the formula (II)

| R¹ | R² |
|---|---|
| cyclohexyl | C₂H₅ |
| cyclohexyl | C₃H₇ |
| cyclopentyl | C₃H₇ |
| CH₃ | cyclopentyl |
| CH₃ | cyclohexyl |
| NH₂ | CH₃ |
| CH₃ | NHCH₃ |
| NHCH₃ | CH₃ |
| NHCH₃ | C₂H₅ |
| NHCH₃ | C₃H₇ |
| N(CH₃)₂ | CH₃ |
| N(CH₃)₂ | C₂H₅ |
| N(CH₃)₂ | C₃H₇ |
| OCH₃ | CH₃ |
| OCH₃ | C₂H₅ |
| OC₂H₅ | CH₃ |
| OC₂H₅ | C₂H₅ |
| cyclopropyl | cyclopropyl |
| cyclopropyl | CH₂—O—C₂H₅ |
| cyclopropyl | N(CH₃)₂ |
| O—C₃H₇ | C₃H₇ |
| cyclopentyl | cyclopropyl |
| cyclohexyl | cyclopropyl |
| O—CH₂—CH=CH₂ | CH₃ |
| O—CH₂—CH=CH₂ | C₂H₅ |
| O—CH₂—CH=CH₂ | C₃H₇ |
| O—CH₂—CH—CH₂—Br<br>           \|<br>           Br | C₃H₇ |
| OCH₃ | cyclopropyl |
| OCH₃ | cyclobutyl |
| OCH₃ | cyclopentyl |
| OCH₃ | cyclohexyl |
| OCH₃ | CH₂—phenyl |
| OCH₃ | N(CH₃)₂ |
| O—CH₂—COOCH₃ | C₃H₇ |
| N(CH₃)₂ | cyclopropyl |
| N(CH₃)₂ | cyclopentyl |
| N(CH₃)₂ | cyclohexyl |
| OC₂H₅ | C₃H₇ |
| OC₂H₅ | cyclopropyl |
| OC₂H₅ | cyclopentyl |
| OC₂H₅ | cyclohexyl |
| cyclopentyl | C₂H₅ |
| NH—CH₃ | CH₂—O—CH₃ |
| cyclopropyl | CH₂—O—CH₃ |
| CH₃ | CH₂—O—CH₃ |

The starting substances of the formula (II) are known and/or can be prepared by processes known per se (cf. Chem. Ber. 90 (1957), 909–921; loc.cit. 98 (1965), 3025–3099; J. Heterocycl. Chem. 15 (1978), 237–240; Tetrahedron 32 (1976), 2347–2352; Helv. Chim. Acta 63 (1980), 841–859; J. Chem.

Soc. C 1967, 746–751; EP-A 283,876; EP-A 294,666; EP-A 301,946; EP-A 298,371; DE-P 3,839,206/LeA 26,538 dated 19.11.1988; DE-P 3,916,207/LeA 26,849 dated 18.05.1989; DE-P 3,916,208/LeA 26,850 dated 18.05.1989; J. Chem. Soc. C 1970, 26–34; DE-P 3,916,930/LEA 26,886 dated 24.05.1989).

For example, the triazolinones of the formula (II) are obtained when

α) oxadiazolinones of the general formula (VII)

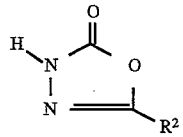
(VII)

in which

R² has the abovementioned meaning are reacted with amino compounds of the general formula (VIII)

(VIII)

in which

R¹ has the abovementioned meaning, at temperatures between 20° C. and 120° C. and, if appropriate, in the presence of a diluent, such as, for example, water, and the hydrazine derivatives formed by this process, of the general formula (IX)

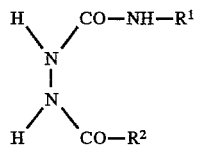
(IX)

in which

R¹ and R² have the abovementioned meanings, are isolated by customary methods (cf. the Preparation Examples) and—or if appropriate even without intermediate isolation—the compounds of the formula (IX) are condensed at temperatures between 20° C. and 120° C. and, if appropriate, in the presence of a basic condensation auxiliary, such as, for example, sodium hydroxide, and, if appropriate, in the presence of a diluent, such as, for example, water, to give the compounds of the formula (II) (cf. EP-A 301,946, DE-OS (German Published Specification) 3,743,493/LEA 25,759 and the Preparation Examples), or when β) amino compounds of the general formula (VIII)

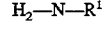
(VIII)

in which

R¹ has the abovementioned meaning, are reacted with carbonic acid derivatives, such as, for example, diphenyl carbonate, then with hydrazine or hydrazine hydrate and eventually with a carboxylic acid derivative or carbonic acid derivative of the general formula (X)

$(RO)_3C—R^2$ (X)

in which

R² has the abovementioned meaning and

R represents lower alkyl, at temperatures between 0° C. and 150° C. and, if appropriate, in the presence of a diluent, such as, for example, ethylene chloride (cf.

DE-P 3,920,270/LeA 26,937 dated 21.06.1989, DE-P 3,928,662/LeA 27,137 dated 30.08.1989, and the Preparation Examples).

The triazolinones of the general formula (IIa)

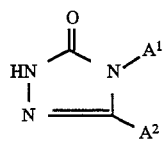
(IIa)

in which

A¹ represents in each case optionally substituted alkyl, alkenyl, cycloalkyl, alkoxy or dialkylamino and A² represents hydrogen, or represents in each case optionally substituted alkyl, cycloalkyl, aralkyl, aryl or alkoxy, provided that both A¹ and A² do not simultaneously represent alkyl, are new and a subject of the present invention.

The new triazolinones of the formula (IIa) are obtained either when oxazolinones of the general formula (VIIa)

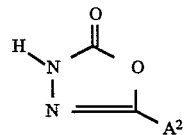
(VIIa)

in which

A² has the abovementioned meaning, are reacted with amino compounds of the general formula (VIIIa)

$H_2N—A^1$ (VIIIa)

in which

A¹ has the abovementioned meaning, analogously to the process described above under (α), or when amino compounds of the general formula (VIIIa)

$H_2N—A^1$ (VIIIa)

are reacted with carbonic acid derivatives, then with hydrazine or hydrazine hydrate and eventually with a carboxylic acid derivative or carbonic acid derivative of the general formula (Xa)

$(RO)_3C—A^2$ (Xa)

in which

A² and R have the abovementioned meanings, analogously to the process described above under (β) (also see the Preparation Examples).

In the general formula (IIa),

A¹ preferably represents $C_1$–$C_6$-alkyl, $C_3$–$C_5$-alkenyl or $C_3$–$C_6$-cycloalkyl, or represents $C_1$–$C_6$-alkoxy which is optionally substituted by fluorine, chlorine, bromine, cyano, $C_1$–$C_4$-alkoxy or $C_1$–$C_4$-alkoxy-carbonyl, in particular methyl, ethyl, allyl, cyclopropyl, methoxy, ethoxy, propoxy or isopropoxy, or represents di-($C_1$–$C_4$-alkyl)-amino, in particular dimethylamino or diethylamino, and A² preferably represents hydrogen, or represents $C_1$–$C_6$-alkyl which is optionally substituted by fluorine, chlorine, bromine, cyano, $C_1$–$C_4$-alkoxy, $C_1$–$C_4$-alkyl-carbonyl or $C_1$–$C_4$-alkoxy-carbonyl, or represents $C_3$–$C_6$-cycloalkyl which is optionally substituted by fluorine, chlorine, bromine and/or $C_1$–$C_4$-alkyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxycarbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl and/or $C_1$–$C_4$ -alkoxy-carbonyl, or represents $C_1$–$C_4$-alkoxy, in particular hydrogen, $C_1$–C4-alkyl which is optionally substituted by fluorine and/or chlorine, methoxy or ethoxy, or represents $C_3$–$C_6$-cycloalkyl, or represents methoxy or ethoxy, provided that both $A^1$ and $A^2$ do not simultaneously represent $C_1$–$C_6$-alkyl.

The compounds of the formulae (VII), (VIIa), (VIII), (VIIIa) and (X) or (Xa) which are to be used as starting substances for the preparation of the triazolinones of the formulae (II) or (IIa) are known (cf. Helv. Chim. Acta 55 (1972), 1174; EP-A 301,946; DE-OS (German Published Specification) 3,743,493).

Formula (III) provides a general definition of the sulphonyl isocyanates further to be used as starting substances in process (a) according to the invention for the preparation of compounds of the formula (I).

In formula (III), $R^3$ preferably, or in particular, has the meaning which has already been mentioned above in connection with the description of the compounds of the formula (I) according to the invention as being preferred, or particularly preferred, for $R^3$.

Examples of the starting substances of the formula (III) which may be mentioned are:

2-fluoro-, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulphinyl-, 2-methylsulphonyl-, 2-dimethylamino-sulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2-isopropoxycarbonyl- phenylsulphonyl isocyanate, 2-fluoro-, 2-chloro-, 2-difluoromethoxy-, 2-trifluorometh-2 -methoxycarbonyl- and 2-ethoxycarbonyl-benzylsulphonyl isocyanate, 2-methoxycarbonyl-3-thienyl-sulphonyl isocyanate, 4-methoxycarbonyl- and 4-ethoxycarbonyl-1-methyl-pyrazol-5-yl-sulphonyl isocyanate.

The sulphonyl isocyanates of the formula (III) are known and/or can be prepared by processes known per se (cf. U.S. Pat. Nos. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (a) according to the invention for the preparation of the new compounds of the formula (I) is preferably carried out using diluents. Suitable diluents in this context are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

In process (a) according to the invention, the reaction temperatures can be varied within a substantial range. In general, the process is carried out at temperatures between 0° C. and 150° C., preferably at temperatures between 10° C. and 80° C.

Process (a) according to the invention is generally carried out under atmospheric pressure.

For carrying out process (a) according to the invention, between 1 and 3 moles, preferably between 1 and 2 moles, of sulphonyl isocyanate of the formula (III) are generally employed per mole of triazolinone of the formula (II).

The reactants can be combined in any desired sequence. The reaction mixture is stirred until the reaction is complete and concentrated, and the crude product which remains in the residue is crystallized using a suitable solvent, such as, for example, diethyl ether. The product of the formula (I) which has been obtained in crystalline form is isolated by filtration with suction.

Formula (IV) provides a general definition of the triazolinone derivatives to be used as starting substances in process (b) according to the invention for the preparation of compounds of the formula (I).

In formula (IV), $R^1$ and $R^2$ preferably, or in particular, have those meanings which have already been mentioned above in connection with the description of the compounds of the formula (I) according to the invention as being preferred, or particularly preferred, for $R^1$ and $R^2$, and Z preferably represents chlorine, $C_1$–$C_4$-alkoxy, benzyloxy or phenoxy, in particular methoxy or phenoxy.

Examples of the starting substances of the formula (IV) which are possible are the compounds of the formula (IV) to be prepared from the compounds of the formula (II) listed in Table 2 and phosgene, methyl chloroformate, benzyl chloroformate, phenyl chloroformate or diphenyl carbonate.

The starting substances of the formula (IV) are known and/or can be prepared by processes known per se (cf. EP-A 283,876; EP-A 294,666; EP-A 298,371.

The triazolinone derivatives of the formula (IV) are obtained for example when triazolinones of the general formula (II)

in which $R^1$ and $R^2$ have the abovementioned meanings, are reacted with carbonic acid derivatives of the general formula (XI)

in which

Z has the abovementioned meaning and $Z^1$ represents a leaving group, such as chlorine, methoxy, benzyloxy or phenoxy, at temperatures between –20° C. and +100° C., if appropriate in the presence of a diluent, such as, for example, tetrahydrofuran, and, if appropriate, in the presence of an acid acceptor, such as, for example, sodium hydride or potassium tert-butylate (cf. the Preparation Examples).

Formula (V) provides a general definition of the sulphonamides further to be used as starting substances in process (b) according to the invention for the preparation of compounds of the formula (I).

In formula (V), $R^3$ preferably, or in particular, has the meaning which has already been mentioned above in connection with the description of the compounds of the formula (I) according to the invention as being preferred, or particularly preferred, for $R^3$.

Examples of the starting substances of the formula (V) which may be mentioned are:

2-fluoro-, 2-chloro-, 2-bromo-, 2-methyl-, 2-methoxy-, 2-trifluoromethyl, 2-difluoro-methoxy-, 2-trifluoromethoxy-, 2-methylthio-, 2-ethylthio-, 2-propylthio-, 2-methylsulphinyl-, 2-methylsulphonyl-, 2-dimethylamino-sulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2-isopropoxycarbonyl-benzenesulphonamide, 2-fluoro-, 2-chloro-, 2-difluoromethoxy-, 2-trifluoromethoxy-, 2-methoxycarbonyl- and 2-ethoxycarbonyl-phenylmethanesulphonamide, 2-methoxycarbonyl-3-thiophenesulphonamide, 4-methoxycarbonyl- and 4-ethoxycarbonyl-1-methyl-pyrazol-5 -sulphonamide.

The sulphonamides of the formula (V) are known and/or can be prepared by processes known per se (cf. U.S. Pat. Nos. 4,127,405, 4,169,719, 4,371,391; EP-A 7,687, 13,480, 21,641, 23,141, 23,422, 30,422, 30,139, 35,893, 44,808, 44,809, 48,143, 51,466, 64,322, 70,041, 173,312).

Process (b) according to the invention for the preparation of the new compounds of the formula (I) is preferably carried out using diluents. Suitable diluents in this context are virtually all inert organic solvents, for example those which have been indicated above in the case of process (a) according to the invention.

Acid acceptors which can be employed in process (b) according to the invention are all acid-binding agents which can customarily be used for reactions of this type. The following are preferably suitable: alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate, potassium carbonate, sodium tert-butylate and potassium tert-butylate, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabi-cyclo-[2,2,2]-octane (DABCO).

When carrying out process (b) according to the invention, the reaction temperatures can be varied within a substantial range. In general, the process is carried out at temperatures between 0° C. and 100° C., preferably at temperatures between 10° C. and 60° C.

In general, process (b) according to the invention is carried out under atmospheric pressure. However, it is also possible to carry out the process under increased or reduced pressure.

For carrying out process (b) according to the invention, the specifically required starting substances are generally employed in approximately equimolar amounts. However, it is also possible to use one of the two specifically employed components in a substantial excess. In general, the reactions are carried out in a suitable diluent in the presence of an acid acceptor, and the reaction mixture is stirred for several hours at the specifically required temperature. Working-up in process (b) according to the invention is carried out in each case by customary methods.

The triazolinones of the formula (II) which are to be used as starting substances in process (c) according to the invention for the preparation of compounds of the formula (I) have already been described as starting substances for process (a) according to the invention.

Formula (VI) provides a general definition of the sulphonamide derivatives further to be used as starting substances in process (c) according to the invention for the preparation of compounds of the formula (I).

In formula (VI), $R^3$ and Z preferably, or in particular, have those meanings which have already been mentioned above in connection with the description of the compounds of the formula (I) or (IV) according to the invention as being preferred, or particularly preferred, for $R^3$ and Z.

Process (c) according to the invention is preferably carried out using diluents. Suitable diluents in this context are the same organic solvents as have been mentioned above in connection with the description of process (a) according to the invention.

If appropriate, process (c) is carried out in the presence of an acid acceptor. Suitable acid-binding agents in this context are the same as have been mentioned above in connection with the description of process (b) according to the invention.

When carrying out process (c) according to the invention the reaction temperatures can be varied within a substantial range. In general, the process is carried out at temperatures between 0° C. and 100° C., preferably at temperatures between 10° C. and 60° C.

In general, process (c) according to the invention is carried out under atmospheric pressure. However, it is also possible to carry out the process under increased or reduced pressure.

For carrying out process (c) according to the invention, the specifically required starting substances are generally employed in approximately equimolar amounts. However, it is also possible to use one of the two specifically employed components in a substantial excess. In general, the reactions are carried out in a suitable diluent in the presence of an acid acceptor, and the reaction mixture is stirred for several hours at the specifically required temperature. Working-up in process (c) according to the invention is carried out in each case by customary methods.

To convert the compounds of the formula (I) into salts, they are stirred with suitable salt formers, such as, for example, sodium hydroxide, sodium methylate, sodium ethylate, potassium hydroxide, potassium methylate or potassium ethylate, ammonia, isopropylamine, dibutylamine or triethylamine, using suitable diluents, such as, for example, water, methanol or ethanol. The salts can be isolated as crystalline products—then if appropriate after concentrating the mixture.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf, meadows and pastures, and for the selective combating of weeds in annual cultures.

The compounds of the formula (I) according to the invention are suitable for combating monocotyledon and dicotyledon weeds both in the pre-emergence and the post-emergence method. They are markedly more effective than, for example, isocarbamide.

To a certain extent, the compounds according to the invention also show a fungicidal action, for example against powdery mildews and against apple scab, and also against *Pyricularia oryzae* on rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the mains aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H, 3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soya beans; furthermore also mixtures with 2,4-dichlorophenoxyacetic acid (2,4-D); 4-(2,4-dichlorophenoxy)-butric acid (2,4-DB); 2,4-dichlorophenoxypropionic acid (2,4-DP); 5-(2-chloro-4-trifluoromethyl-phenoxy)-2-nitrobenzoic acid (ACIFLUORFEN); 2-chloro-2',6'-diethyl-N-methoxymethyl-acetanilide (ALACHLOR); 2-chloro-4-ethylamino-6-isopropylamino-1,3,5-triazine (ATRAZINE); methyl 2-[[[[(4,6-dimethoxypyrimidin-2-yl)-amino]carbonyl]-amino]-sulphonyl]-methyl]-benzoate (BENSULFURON); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxybenzonitrile; (BROMOXYNIL); N-(butoxymethyl)-2-chloro-N-(2,6-diethyl-phenyl)-acetamide (BUTACHLOR); ethyl 2-{[(4-chloro-6-methoxy-2-pyrimidinyl)-aminocarbonyl]-aminosulphonyl}-benzoate (CHLORIMURON);2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methyl-phenyl)-urea(CHLORTOLURON); 2-chloro-4-ethylamino-6-(3-cyanopropylamino)-1,3,5-triazine (CYANAZINE); 2,6-dichlorobenzonitrile (DICHLOBENIL); 2-[4-(2,4-dichlorophenoxy)phenoxy]- propionic acid, its methyl ester or its ethyl ester (DICLOFOP); 2-[(2-chlorophenyl)-methyl]-4,4-dimethylisoxazolidin-3-one (DIMETHAZONE); 4-amino-6-t-butyl-3-ethylthio-1,2,4-triazin-5(4H)-one (ETHIOZIN); 2-{4-[6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); N,N-dimethyl-N'-(3-trifluoromethylphenyl)-urea (FLUOMETURON); 1-methyl-3-phenyl-5-(3-trifluoromethylphenyl)-4-pyridone (FLURIDONE); 5-(2-chloro-4-trifluoromethyl-phenoxy)-N-methylsulphonyl-2-nitrobenzamide (FOMESAFEN); N-phos-phonomethyl-glycine (GLYPHOSATE); methyl 2-[4,5-dihydro-4-methyl-4-(1-methylethyl)-5 -oxo-1H-imidazol-2-yl]-4(5)-methylbenzoate (IMAZAMETHABENZ); 2-(4,5-dihydro-4-methyl-4-isopropyl-5-oxo-1H-imidazol-2-yl)-pyridine-3-carboxylic acid (IMAZAPYR); 2-[5-methyl-5-(1-methylethyl)-4-oxo-2-imidazolin-2-yl]-3-quinolin-carboxylic acid (IMAZAQUIN); 2-[4,5-dihydro-4-methyl-4-isopropyl-5-oxo-(1H)-imidazol-2-yl]-5-ethylpyridin-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); (2-methyl-4-chloro-phenoxy)-acetic acid (MCPA); (4-chloro-2-methylphenoxy)-propionic acid (MCPP); N-methyl-2-(1,3-benzothiazol-2-yloxy)-acetanilide(MEFENACET); 2-chloro-N-(2,6-dimethyl-phenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); 2-{[ [((4-methoxy-6-methyl-1,3,5-triazin-2-yl)-amino)-carbonyl]-amino]-sulphonyl}-benzoic aicd or its methyl ester (METSULFURON); 1-(3-trifluoromethyl-phenyl)-4-methyl-amino-5-chloro-6-pyridazone (NORFLURAZON); N-(1-ethylpropyl)-3,4-dimethyl-2,6-dinitroaniline (PENDIMETHALIN); 0-(6-chloro-3-phenyl-pyridazin-4-yl) S-octyl thiocarbamate (PYRIDATE); ethyl 2-[4-(6-chloro-quinoxalin-2-yl-oxy)-phenoxy]-propionate (QUIZALOFOP-ETHYL); 2-[1-(ethoxamino)-butylidene]-5-(2-ethylthiopropyl)-1,3-cyclohexadione (SETHOXYDIM); methyl 2-{[(4,6-dimethyl-2-pyrimidinyl)-aminocarbonyl]-aminosulphonyl}-benzoate (SULFOMETURON); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-(2,3,3-trichloroallyl)-N,N-diisopropylthiocarbamate (TRI-ALLATE), 2,6-dinitro-4-trifluoromethyl-N,N-dipropylaniline (TRIFLURALIN). Suprisingly, some mixtures also show a synergistic effect.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

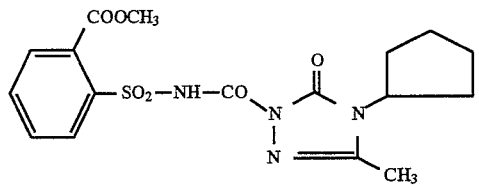

(Process (a))

3.0 g (17.95mmol) of 4-cyclopentyl-5-methyl-2,4-dihydro-3H-1,2,4-triazol-3-one are dissolved in 60 ml of acetonitrile, and 6.9 g (28.6 mmol) of 2-methoxycarbonyl-phenylsulphonyl isocyanate, dissolved in 20 ml of acetonitrile, are added to this solution with stirring. The reaction mixture is stirred for 6 hours at 20° C. and then concentrated. The residue which remains is stirred with diethyl ether, and the product which has been obtained in crystalline form is isolated by filtration with suction.

This gives 6.6 g (90% of theory) of 4-cyclopentyl-5-methyl-2-(2-methoxycarbonyl-phenylsulphonyl-aminocarbonyl)-2,4-dihydro-3H-1,2,4-triazol-3-one of melting point 146° C.

EXAMPLE 2

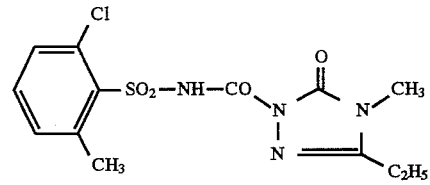

(Process (b))

1.8 g (11.8 mmol) of 1,8-diazabicyclo-[5,4,0]-undec-7-ene (DBU) are added to a stirred mixture of 3.0 g (12.1 mmol) of 5-ethyl-4-methyl-2-phenoxycarbonyl-2,4-dihydro-3H-1,2,4-triazol-3-one, 2.5 g (12.2 mmol) of 2-chloro-6-methyl-benzenesulphonamide and 60 ml of acetonitrile. The reaction mixture is stirred for 2 hours at 20° C., then poured into about twice the volume of ice-water, and a pH of about 2 is established by dropwise addition of concentrated hydrochloric acid. The product which has been obtained during this process in crystalline form is isolated by filtration with suction.

This gives 3.2 g (73.5% of theory) of 5-ethyl-4-methyl-2-(2-chloro-6-methyl-phenylsulphonyl-aminocarbonyl)-2,4-dihydro-3H-1,2,4-triazol-3-one of melting point 176° C.

For example the compounds of the formula (I) listed in Table 3 below can also be prepared analogously to Examples 1 and 2 and following the general instructions of the preparation processes according to the invention.

TABLE 3
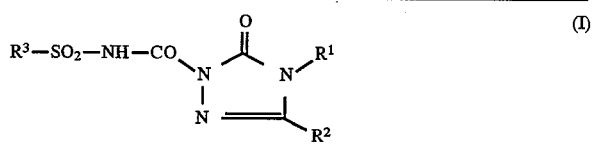
Preparation Examples of the compounds of the formula (1) (m.p. = melting point):
| Ex. No. | $R^1$ | $R^2$ | $R^3$ | m.p. (°C.) |
|---|---|---|---|---|
| 3 | $C_6H_5$ | $CH_3$ | 2-($COOCH_3$)-phenyl | 158 |
| 4 | $CH_3$ | $C_2H_5$ | 2-($OCHF_2$)-phenyl | 159 |
| 5 | $C_2H_5$ | $C_2H_5$ | 2-($OCHF_2$)-phenyl | 115 |
| 6 | $CH_3$ | $C_3H_7$ | 2-($OCHF_2$)-phenyl | 143 |
| 7 | $C_2H_5$ | $C_2H_5$ | 2-Cl-3-$CH_3$-phenyl | 139 |
| 8 | $CH_3$ | $C_3H_7$ | 2-Cl-3-$CH_3$-phenyl | 141 |
| 9 | $OCH_3$ | $CH_3$ | 2-($COOCH_3$)-phenyl | 121 |
| 10 | $OCH_3$ | $CH_3$ | 2-($SO_2N(CH_3)_2$)-phenyl | 180 |

TABLE 3-continued $$R^3-SO_2-NH-CO-N(-N=C(R^2))-CO-NR^1$$ (I)

Preparation Examples of the compounds of the formula (1) (m.p. = melting point):

| Ex. No. | R¹ | R² | R³ | m.p. (°C.) |
|---|---|---|---|---|
| 11 | OCH₃ | CH₃ | 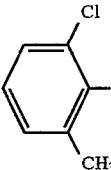 2-Cl, 3-CH₃-phenyl | 149 |
| 12 | OCH₃ | C₂H₅ | 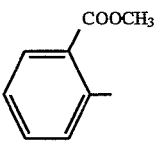 2-COOCH₃-phenyl | 144 |
| 13 | OCH₃ | C₃H₇ | 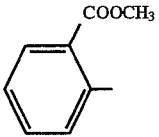 2-COOCH₃-phenyl | 128 |
| 14 | CH₃ | C₂H₅ | 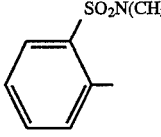 2-SO₂N(CH₃)₂-phenyl | 173 |
| 15 | CH₃ | C₃H₇ | 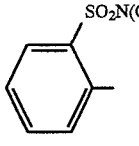 2-SO₂N(CH₃)₂-phenyl | 133 |
| 16 |  cyclopropyl | C₂H₅ | 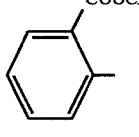 2-COOCH₃-phenyl | 154 |
| 17 | OCH₃ | CH(CH₃)₂ | 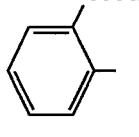 2-COOCH₃-phenyl | 137 |
| 18 |  cyclopropyl | C₂H₅ | 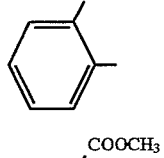 2-SO₂N(CH₃)₂-phenyl | 174 |
| 19 |  cyclopropyl | C₃H₇ | 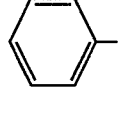 2-COOCH₃-phenyl | 97 |

TABLE 3-continued $$R^3-SO_2-NH-CO-N-C(=O)-N(R^1)-N=C(R^2)$$ (I)

Preparation Examples of the compounds of the formula (1) (m.p. = melting point):

| Ex. No. | $R^1$ | $R^2$ | $R^3$ | m.p. (°C.) |
|---|---|---|---|---|
| 20 | $CH_3$ | $N(CH_3)_2$ | 2-($COOCH_3$)$C_6H_4$ | 168 |
| 21 | $OCH_2C_6H_5$ | $CH_3$ | 2-($COOCH_3$)$C_6H_4$ | 174 |
| 22 | $C_2H_5$ | $C_3H_7$ | 2-Cl-3-$CH_3$-$C_6H_3$ | 136 |
| 23 | $N(CH_3)_2$ | $C_2H_5$ | 2-($COOCH_3$)$C_6H_4$ | 139 |
| 24 | $N(CH_3)_2$ | H | 2-($COOCH_3$)$C_6H_4$ | 197 |
| 25 | $N(CH_3)_2$ | $CH(CH_3)_2$ | 2-($COOCH_3$)$C_6H_4$ | 148 |
| 26 | $OC_2H_5$ | $C_2H_5$ | 2-($COOCH_3$)$C_6H_4$ | 153 |
| 27 | $OC_2H_5$ | $C_3H_7$ | 2-($COOCH_3$)$C_6H_4$ | 155 |
| 28 | cyclopropyl | $CH(CH_3)_2$ | 2-($COOCH_3$)$C_6H_4$ | 186 |

TABLE 3-continued $$R^3-SO_2-NH-CO-N(-N=)-CO-N(R^1)(R^2) \quad (I)$$

Preparation Examples of the compounds of the formula (1) (m.p. = melting point):

| Ex. No. | $R^1$ | $R^2$ | $R^3$ | m.p. (°C.) |
|---|---|---|---|---|
| 29 | cyclopropyl | $C_3H_7$ | 2-Cl-3-CH_3-phenyl | 146 |
| 30 | $N(CH_3)_2$ | $C_3H_7$ | 2-COOCH_3-phenyl | 110 |
| 31 | $N(CH_3)_2$ | cyclopropyl | 2-COOCH_3-phenyl | 131 |
| 32 | $C_2H_5$ | $C_4H_9$ | 2-COOCH_3-phenyl | 98 |
| 33 | $CH_3$ | $C_4H_9$ | 2-COOCH_3-phenyl | 113 |
| 34 | $C_3H_7$ | $C_4H_9$ | 2-COOCH_3-phenyl | 88 |
| 35 | cyclopropyl | $C_4H_9$ | 2-COOCH_3-phenyl | 117 |
| 36 | $OCH_3$ | $C_4H_9$ | 2-COOCH_3-phenyl | 117 |
| 37 | $CH_3$ | cyclopropyl | 2-COOCH_3-phenyl | 141 |

TABLE 3-continued $$R^3-SO_2-NH-CO-N(CO-N R^1)-N=C R^2$$ (I)

Preparation Examples of the compounds of the formula (1) (m.p. = melting point):

| Ex. No. | R$^1$ | R$^2$ | R$^3$ | m.p. (°C.) |
|---|---|---|---|---|
| 38 | C$_2$H$_5$ | cyclopropyl | 2-COOCH$_3$-phenyl | 130 |
| 39 | C$_3$H$_7$ | cyclopropyl | 2-COOCH$_3$-phenyl | 139 |
| 40 | cyclopropyl | cyclopropyl | 2-COOCH$_3$-phenyl | 151 |
| 41 | cyclohexyl, H | CH$_3$ | 2-COOCH$_3$-phenyl | 151 |
| 42 | CH(CH$_3$)$_2$ | NHCH(CH$_3$)$_2$ | 2-COOCH$_3$-phenyl | 135 |
| 43 | N(CH$_3$)$_2$ | N(CH$_3$)$_2$ | 2-COOCH$_3$-phenyl | 171 |
| 44 | CH$_3$ | C$_3$H$_7$ | 2-OCF$_3$-phenyl | 168 |
| 45 | C$_2$H$_5$ | N(CH$_3$)$_2$ | 2-COOCH$_3$-phenyl | 134 |
| 46 | CH$_3$ | C$_2$H$_5$ | 2-OCF$_3$-phenyl | 167 |

TABLE 3-continued

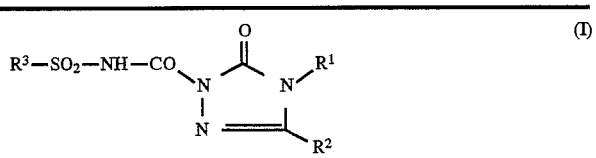

(I)

Preparation Examples of the compounds of the formula (1) (m.p. = melting point):

| Ex. No. | $R^1$ | $R^2$ | $R^3$ | m.p. (°C.) |
|---|---|---|---|---|
| 47 | $NH_2$ | $C_3H_7$ | 2-$OCF_3$-phenyl | 120 |
| 48 | cyclohexyl | NH-cyclohexyl | 2-$COOCH_3$-phenyl | 120 |
| 49 | cyclopropyl | H | 2-$COOCH_3$-phenyl | 195 |
| 50 | $-CH_2CH=CH_2$ | $C_2H_5$ | 2-$COOCH_3$-phenyl | 108 |
| 51 | $-CH_2CH=CH_2$ | H | 2-$COOCH_3$-phenyl | 158 |
| 52 | $OCH_3$ | $C_3H_7$ | 2-$OCF_3$-phenyl | 110–111 |
| 53 | $-CH_2$-phenyl | H | 2-$COOCH_3$-phenyl | 212–214 |
| 54 | $C_3H_7$ | H | 2-$COOCH_3$-phenyl | 168–169 |
| 55 | cyclopropyl | $C_3H_7$ | 2-$OCF_3$-phenyl | 103–105 |

TABLE 3-continued
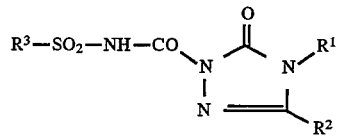 (I)
Preparation Examples of the compounds of the formula (1) (m.p. = melting point):
| Ex. No. | R¹ | R² | R³ | m.p. (°C.) |
|---|---|---|---|---|
| 56 |  | $C_2H_5$ | 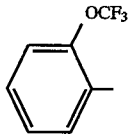 (OCF₃) | 127 |
| 57 | OCH₃ | $C_2H_5$ | 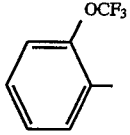 (OCF₃) | 111–113 |
| 58 | —OCH₃ |  | 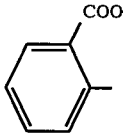 (COOCH₃) | 139 |
| 59 | —NHCH₃ | $C_3H_7$-n | 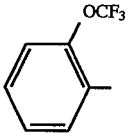 (OCF₃) | 196 |
| 60 | CH₃ | $C_3H_7$-n | 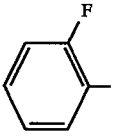 (F) | 178 |
| 61 | 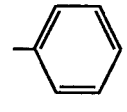 | H | 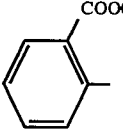 (COOCH₃) | 177 |
| 62 | —CH₂CH(CH₃)₂ | $C_2H_5$ | 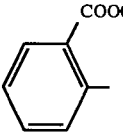 (COOCH₃) | 123 |
| 63 | —CH₂CH=CH₂ | $C_3H_7$-n | 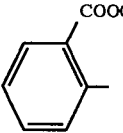 (COOCH₃) | (amorphous) |
| 64 | 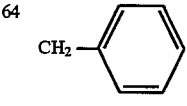 (CH₂—) | $C_2H_5$ | 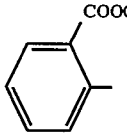 (COOCH₃) | 157 |

TABLE 3-continued $$R^3-SO_2-NH-CO-N\underset{N=\underset{R^2}{\overset{|}{C}}}{\overset{\overset{O}{\parallel}}{C}}-N\overset{R^1}{\underset{}{}}$$ (I)

Preparation Examples of the compounds of the formula (1) (m.p. = melting point):

| Ex. No. | $R^1$ | $R^2$ | $R^3$ | m.p. (°C.) |
|---|---|---|---|---|
| 65 | 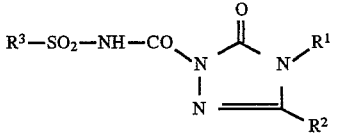 phenyl | $C_2H_5$ | 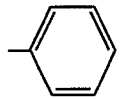 2-COOCH$_3$-phenyl | 117 |
| 66 | $-C(CH_3)_3$ | $C_2H_5$ | 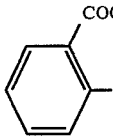 2-COOCH$_3$-phenyl | 182 |
| 67 | 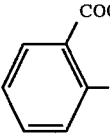 cyclobutyl | $C_2H_5$ | 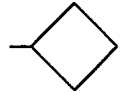 2-COOCH$_3$-phenyl | 133 |
| 68 | 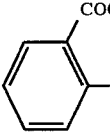 cyclopentyl | $C_2H_5$ | 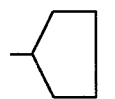 2-COOCH$_3$-phenyl | 162 |
| 69 | $-CH_2-CH=CH_2$ | $CH_3$ | 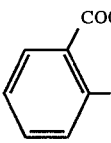 2-COOCH$_3$-phenyl | 120 |
| 70 | 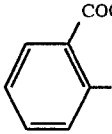 cyclohexyl | $C_2H_5$ | 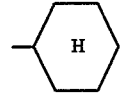 2-COOCH$_3$-phenyl | 183 |
| 71 | $C_2H_5$ | H | 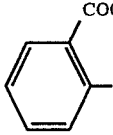 2-COOCH$_3$-phenyl | 196 |
| 72 | 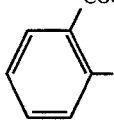 cyclobutyl | $CH_3$ | 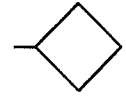 2-COOCH$_3$-phenyl | 153 |
| 73 | $-OCH_3$ | 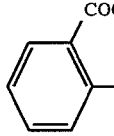 cyclopropyl |  2-OCF$_3$-phenyl | 138 |

TABLE 3-continued

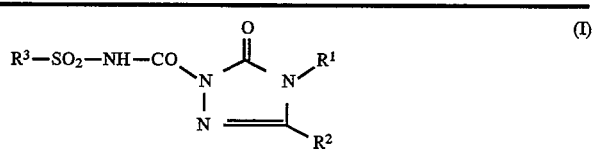

Preparation Examples of the compounds of the formula (1) (m.p. = melting point):

| Ex. No. | $R^1$ | $R^2$ | $R^3$ | m.p. (°C.) |
|---|---|---|---|---|
| 74 | $CH(CH_3)_2$ | H | 2-$COOCH_3$-phenyl | 191 |
| 75 | cyclopentyl | H | 2-$COOCH_3$-phenyl | 191 |
| 76 | cyclohexyl | H | 2-$COOCH_3$-phenyl | 192 |
| 77 | $-C(CH_3)_3$ | H | 2-$COOCH_3$-phenyl | 211 |
| 78 | $-CH_2-CH(Br)-CH_2Br$ | $CH_3$ | 2-$COOCH_3$-phenyl | 110 |
| 79 | $CH_3$ | $-CH_2OCH_3$ | 2-$COOCH_3$-phenyl | 152 |
| 80 | $CH_3$ | $C_2H_5$ | 2-F-phenyl | 174 |
| 81 | $CH_3$ | $-CH_2OC_2H_5$ | 2-$COOCH_3$-phenyl | 123 |
| 82 | $-OCH_3$ | $C_3H_7$-n | 2-$CF_3$-phenyl | (amorphous) |

TABLE 3-continued

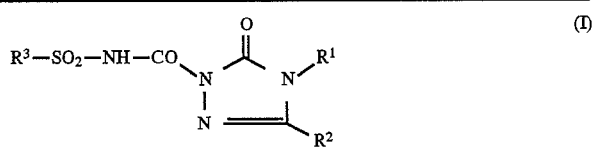

Preparation Examples of the compounds of the formula (1) (m.p. = melting point):

| Ex. No. | R¹ | R² | R³ | m.p. (°C.) |
|---|---|---|---|---|
| 83 | cyclopropyl | C₂H₅ | 2-methyl-3-(CON(CH₃)₂)-pyridin-yl | 124 |
| 84 | cyclopropyl | —CH₂OCH₃ | 2-OCF₃-phenyl | 102 |
| 85 | cyclopropyl | —CH₂OCH₃ | 2-COOCH₃-phenyl | 155 |
| 86 | cyclopropyl | —CH₂OC₂H₅ | 2-COOCH₃-phenyl | 123 |
| 87 | cyclopropyl | —CH₂OC₂H₅ | 2-OCF₃-phenyl | 99 |
| 88 | cyclopropyl | —N(CH₃)₂ | 2-Cl-6-CH₃-phenyl | 189 |
| 89 | —OCH₃ | C₂H₅ | 2-Cl-6-CH₃-phenyl | 155 |
| 90 | cyclopropyl | C₂H₅ | 2-Cl-6-CH₃-phenyl | 133 |

TABLE 3-continued
Preparation Examples of the compounds of the formula (1) (m.p. = melting point):
| Ex. No. | R¹ | R² | R³ | m.p. (°C.) |
|---|---|---|---|---|
| 91 | —OCH$_3$ | C$_3$H$_7$-n | 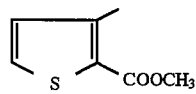 | 125 |
| 92 | 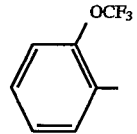 | C$_2$H$_5$ | 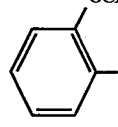 | 138 |
| 93 | —OC$_2$H$_5$ | C$_2$H$_5$ | 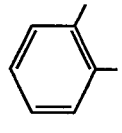 | 132 |
| 94 | —OC$_2$H$_5$ | C$_3$H$_7$-n | 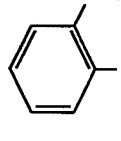 | 107 |
| 95 | —OCH$_3$ | CH(CH$_3$)$_2$ |  | 128 |
| 96 | OCH$_3$ | CH$_3$ | 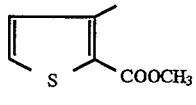 | 119 |
| 97 |  | C$_3$H$_7$-n | 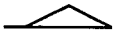 | 100 |
| 98 | 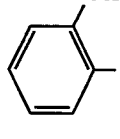 | 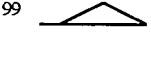 | 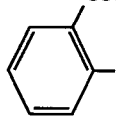 | 140 |
| 99 |  | —N(CH$_3$)$_2$ |  | 163 |

TABLE 3-continued $$R^3-SO_2-NH-CO-N\overset{O}{\underset{\underset{N}{|}}{\diagdown}}\overset{\diagup}{\underset{\diagdown}{N}}\overset{R^1}{\underset{R^2}{\diagup}}$$ (I)

Preparation Examples of the compounds of the formula (1) (m.p. = melting point):

| Ex. No. | R¹ | R² | R³ | m.p. (°C.) |
|---|---|---|---|---|
| 100 | △ | —N(CH₃)₂ | 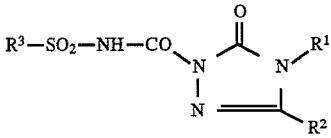 2-CH₃-C₆H₄ | 182 |
| 101 | CH₃ | —N(CH₃)₂ |  2-Cl-6-CH₃-C₆H₃ | 181 |
| 102 | CH₃ | —OCH₃ | 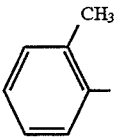 2-COOCH₃-C₆H₄ | 150 |
| 103 | C₂H₅ | △ | 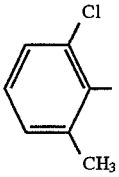 2-Cl-6-CH₃-C₆H₃ | 147 |
| 104 | —CH₂—CH=CH₂ | CH₃ | 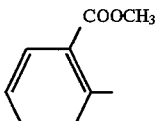 2-Cl-6-CH₃-C₆H₃ | 132 |
| 105 | —CH₂—CH=CH₂ | C₂H₅ |  2-Cl-6-CH₃-C₆H₃ | 109 |
| 106 | —CH₂—CH=CH₂ | C₃H₇-n | 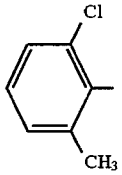 2-Cl-6-CH₃-C₆H₃ | 104 |

TABLE 3-continued
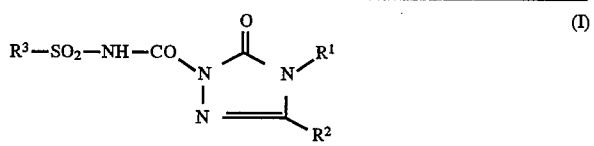
Preparation Examples of the compounds of the
formula (1) (m.p. = melting point):
| Ex. No. | R¹ | R² | R³ | m.p. (°C.) |
|---|---|---|---|---|
| 107 | —OC₂H₅ | C₂H₅ | 2-Cl-3-CH₃-phenyl | 147 |
| 108 | —OC₂H₅ | C₃H₇-n | 2-Cl-3-CH₃-phenyl | 136 |
| 109 | —OCH₃ | CH(CH₃)₂ | 2-Cl-3-CH₃-phenyl | 126 |
| 110 | CH₃ | CH₃ | 2-Cl-3-CH₃-phenyl | 146 |
| 111 | cyclopropyl | CH₃ | 2-Cl-3-CH₃-phenyl | 175 |
| 112 | CH₃ | CH(CH₃)₂ | 2-Cl-3-CH₃-phenyl | 124 |
| 113 | CH₃ | cyclopropyl | 2-Cl-3-CH₃-phenyl | 171 |

TABLE 3-continued $$R^3-SO_2-NH-CO-N(-N=CR^2R^1\text{-aminocarbonyl-triazolone})\quad (I)$$

Preparation Examples of the compounds of the formula (1) (m.p. = melting point):

| Ex. No. | $R^1$ | $R^2$ | $R^3$ | m.p. (°C.) |
|---|---|---|---|---|
| 114 | cyclopropyl | $CH(CH_3)_2$ | 2-Cl-6-CH$_3$-phenyl | 132 |
| 115 | cyclopropyl | cyclopropyl | 2-Cl-6-CH$_3$-phenyl | 167 |
| 116 | $CH_3$ | $CH_3$ | 2-CH$_3$-phenyl | 155 |
| 117 | $CH_3$ | $C_2H_5$ | 2-CH$_3$-phenyl | 147 |
| 118 | $CH_3$ | $C_3H_7$-n | 2-CH$_3$-phenyl | 169 |
| 119 | $OCH_3$ | $C_2H_5$ | 3-methyl-2-(methoxycarbonyl)thiophene |  |
| 120 | $-CH_2-$(2,2-dichlorocyclopropyl) | $C_2H_5$ | 2-COOCH$_3$-phenyl | 132 |

EXAMPLE 121

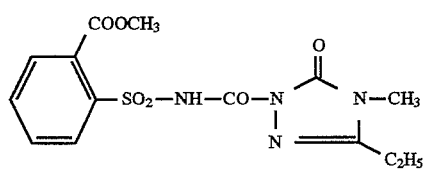

A mixture of 3.8 g (0.03 mol) of 5-ethyl-4-methyl-2,4-dihydro-3H-1,2,4-triazol-3-one, 12 g (0.05 mol) of 2-methoxy-carbonyl-phenylsulphonyl isocyanate and 50 ml of methylene chloride is stirred at 20° C. for 20 hours and then evaporated under a waterpump vacuum. The residue is triturated with diethyl ether, and the crystalline product which is obtained during this process is isolated by filtering off with suction.

6 g (54% of theory) of 5-ethyl-4-methyl-2-(2-methoxycarbonyl-phenylsulphonyl-aminocarbonyl)-2,4-dihydro-3H-1,2,4-triazol-3-one of melting point 131° C. are obtained.

In analogy to Example 121 and following the general description of the preparation process according to the invention, for example the compounds of the formula (I) which are listed in Table 3 below can be prepared.

Table 3 - continuation $$R^3-SO_2-NH-CO-N\underset{N}{\overset{\underset{\displaystyle\|}{O}}{\overset{\displaystyle\|}{\underset{\|}{C}}}}\underset{R^2}{N-R^1}$$ (I)

| Ex. No. | R¹ | R² | R³ | m.p. (°C.) |
|---|---|---|---|---|
| 122 | C₂H₅ | H | 2-Cl-C₆H₄- | 118 |
| 123 | CH₃ | CH₃ | 2-Cl-C₆H₄- | 172 |
| 124 | CH₃ | C₂H₅ | 2-OCF₃-C₆H₄-CH₂- | 122 |
| 125 | CH₃ | CH₂CH₂OCH₃ | 2-COOCH₃-C₆H₄- | amorphous |
| 126 | CH₃ | C₂H₅ | 2-Br-C₆H₄- | 164 |
| 127 | C₂H₅ | C₂H₅ | 2-Cl-C₆H₄- | 172 |
| 128 | CH₃ | C₃H₇-n | 2-Cl-C₆H₄- | 132 |
| 129 | C₂H₅ | C₃H₇-n | 2-Cl-C₆H₄- | 153 |
| 130 | CH(CH₃)₂ | C₃H₇-n | 2-Cl-C₆H₄- | 157 |

-continued
Table 3 - continuation
$$R^3-SO_2-NH-CO-N\begin{array}{c}O\\||\\\diagdown\end{array}N-R^1 \quad (I)$$
| Ex. No. | $R^1$ | $R^2$ | $R^3$ | m.p. (°C.) |
|---|---|---|---|---|
| 131 | $CH_3$ | $C_2H_5$ | 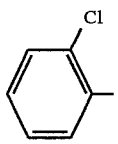 2-Cl-phenyl | 200 |
| 132 | $C_2H_5$ | $CH_3$ | 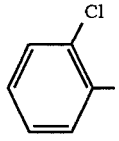 2-Cl-phenyl | 173 |
| 133 | $C_2H_5$ | $C_2H_5$ | 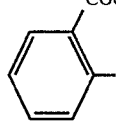 2-COOCH$_3$-phenyl | 207 |
| 134 | $CH(CH_3)_2$ | $CH_3$ | 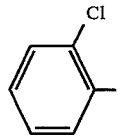 2-Cl-phenyl | 127 |
| 135 | $CH(CH_3)_2$ | $CH(CH_3)_2$ | 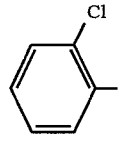 2-Cl-phenyl | 142 |
| 136 | $CH(CH_3)_2$ | $C_2H_5$ | 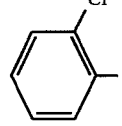 2-Cl-phenyl | 112 |
| 137 | $CH_3$ | $CH(CH_3)_2$ | 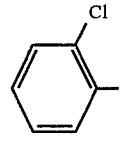 2-Cl-phenyl | 125 |
| 138 | $C_2H_5$ | $CH(CH_3)_2$ | 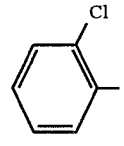 2-Cl-phenyl | 250 |
| 139 | $C_3H_7$-n | $CH(CH_3)_2$ | 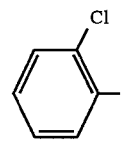 2-Cl-phenyl | 255 |

-continued

Table 3 - continuation $$R^3-SO_2-NH-CO-N \begin{array}{c} \overset{O}{\underset{\|}{C}} \\ | \\ N \end{array} \begin{array}{c} N-R^1 \\ \| \\ R^2 \end{array} \quad (I)$$

| Ex. No. | R¹ | R² | R³ | m.p. (°C.) |
|---|---|---|---|---|
| 140 | CH(CH₃)₂ | CH₃ | 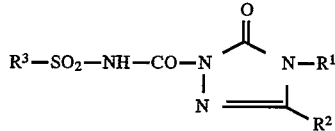 2-COOCH₃-C₆H₄ | 165 |
| 141 | C₃H₇ | CH₃ | 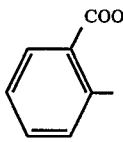 2-COOCH₃-C₆H₄ | 180 |
| 142 | C₃H₇-n | C₂H₅ | 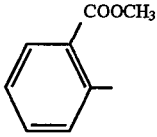 2-COOCH₃-C₆H₄ | 187 |
| 143 | CH(CH₃)₂ | C₂H₅ | 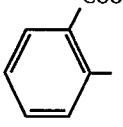 2-COOCH₃-C₆H₄ | 133 |
| 144 | CH₃ | C₃H₇-n | 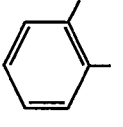 2-COOCH₃-C₆H₄ | 225 |
| 145 | C₂H₅ | C₃H₇-n | 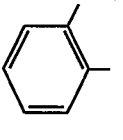 2-COOCH₃-C₆H₄ | 173 |
| 146 | C₃H₇-n | C₃H₇-n | 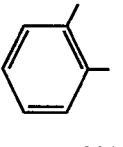 2-COOCH₃-C₆H₄ | 143 |
| 147 | CH(CH₃)₂ | C₃H₇-n | 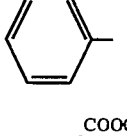 2-COOCH₃-C₆H₄ | 120 |
| 148 | CH₃ | CH(CH₃)₂ | 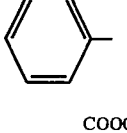 2-COOCH₃-C₆H₄ | 147 |

-continued

Table 3 - continuation $$R^3-SO_2-NH-CO-N\overset{\underset{N}{\parallel}}{\underset{\phantom{N}}{\diagdown}}\overset{O}{\overset{\parallel}{C}}\diagup N-R^1 \qquad (I)$$
$$\phantom{R^3-SO_2-NH-CO-N}\diagdown\!\!=\!\!\diagup R^2$$

| Ex. No. | R¹ | R² | R³ | m.p. (°C.) |
|---|---|---|---|---|
| 149 | C₂H₅ | CH(CH₃)₂ | 2-COOCH₃-C₆H₄ | 187 |
| 150 | C₃H₇-n | CH(CH₃)₂ | 2-COOCH₃-C₆H₄ | 78 |
| 151 | CH(CH₃)₂ | CH(CH₃)₂ | 2-COOCH₃-C₆H₄ | 167 |
| 152 | CH₃ | C₂H₅ | 2-COOCH₃-C₆H₄ | 144 |
| 153 | CH₃ | CH₃ | 2-COOCH₃-C₆H₄ | 133 |
| 154 | C₂H₅ | CH₃ | 2-COOCH₃-C₆H₄ | 141 |
| 155 | cyclopropyl | CH₃ | 2-COOCH₃-C₆H₄ | 144 |
| 156 | C₆H₅-CH₂- | CH₃ | 2-COOCH₃-C₆H₄ | 173 |
| 157 | —N(CH₃)₂ | CH₃ | 2-COOCH₃-C₆H₄ | 165 |

STARTING SUBSTANCES OF THE FORMULA (II)

EXAMPLE (II-1)

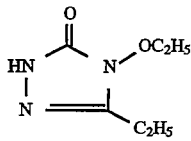

Step 1:

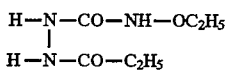       (IX-1)

A mixture of 68.5 g (0.60 mol) of 5-methyl-1,3,4-oxadiazolin-2-one, 45.8 g (0.75 mol) of 0-ethylhydroxylamine and 400 ml of water is refluxed for 12 hours and then concentrated. The residue is taken up in ethanol and reconcentrated. The residue which is obtained in this process is stirred with diethyl ether, and the product which has been obtained in crystalline form is isolated by filtration with suction.

This gives 77.5 g (74% of theory) of 1-ethoxyaminocarbonyl-2-propionyl-hydrazine of melting point 122° C.

Step 2:

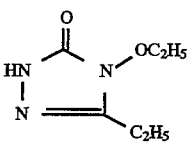       (II-1)

A mixture of 75.5 g (0.43 mol) of 1-ethoxyaminocarbonyl-2-propionyl-hydrazine, 17.5 g (0.44 mol) of sodium hydroxide and 300 ml of water is refluxed for 12 hours. When the mixture is cold, a ph of between 3 and 4 is established by adding concentrated hydrochloric acid, and the mixture is concentrated. The residue is stirred with ethyl acetate, and the sodium chloride which has remained undissolved is separated off by filtration with suction. The filtrate is concentrated, the residue is stirred with diethyl ether, and the product which has been obtained in crystalline form is isolated by filtration with suction.

This gives 37 g (55% of theory) of 4-ethoxy-5-ethyl-2,4-dihydro-3H-1,2,4-triazol-3-one of melting point 93° C.

EXAMPLE (II-2)

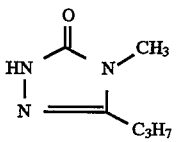       (II-2)

A mixture of 40 g (0.31 mol) of 5-propyl-1,3,4-oxadiazolin-2-one, 109 g of aqueous methylamine solution (32% strength, 1.125 mol of $CH_3NH_2$) and 500 ml of water is refluxed for 12 hours and then concentrated. The residue is taken up in ethanol and reconcentrated. The residue obtained in this process is stirred with diethyl ether, and the product which has been obtained in crystalline form is isolated by filtration with suction.

This gives 31.7 g (72% of theory) of 4-methyl-5-propyl-2,4-dihydro-3H-1,2,4-triazol-3-one of melting point 86° C.

EXAMPLE (II-3)

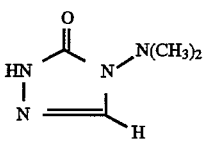

856 g (4.0 mol) of diphenyl carbonate are dissolved in 588 g of ethylene chloride. 245 g (4.0 mol) of dimethylhydrazine (98% pure) are added dropwise with water-cooling, and the mixture is heated slowly and, for 4 hours, stirred at 60° C.

After the mixture has cooled to 20° C., 200 g (4.0 mol) of hydrazine hydrate are added dropwise, and the mixture is then stirred for 12 hours. It is warmed to 70°–80° C. and, for about 1 hour, stirring is continued. When cold, the solution is distilled in vacuo, during which process ethylene chloride and water are removed (final bottom temperature 100° C.). The above phenolic dimethyl carbodihydrazide solution is added dropwise in the course of 90 minutes at reflux temperature (about 102° C.) to 424 g (4.0 mol) of trimethyl orthoformate. After the methanol which has formed is removed by distillation, phenol is distilled off in vacuo, after which 282 g of product mixture are obtained at a head temperature of 85°–105° C. This mixture is boiled with 600 ml of acetone, and filtered at boiling point, and the filtrate is then cooled. The product which has been obtained in this process in crystalline form is isolated by filtration with suction.

This gives 71 g (14% of theory) of 4-dimethylamino-2,4-dihydro-3H-1,2,4-triazol-3-one of melting point 127° C.

For example the compounds of the formulae (II) and (IIa) listed in Table 4 below can also be prepared analogously to Examples (II-1) to (II-3).

TABLE 4

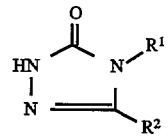       (II)

Preparation examples of the compounds of the formula (II)

| Ex. No. | $R^1$ | $R^2$ | m.p. (°C.) |
|---|---|---|---|
| II-4 | $C_3H_7$ | $CH_3$ | 48 |
| II-5 | $CH(CH_3)_2$ | $CH_3$ | 118 |
| II-6 | $CH_3$ | $CH_3$ | 139 |
| II-7 | $C_2H_5$ | $C_2H_5$ | 117 |
| II-8 | $C_3H_7$ | $C_2H_5$ | 42–45 |
| II-9 | $CH(CH_3)_2$ | $C_2H_5$ | 102 |
| II-10 | $C_2H_5$ | $C_3H_7$ | 97 |
| II-11 | $C_3H_7$ | $C_3H_7$ | (amorphous) |
| II-12 | $CH(CH_3)_2$ | $C_3H_7$ | 91 |
| II-13 | $CH_3$ | $CH(CH_3)_2$ | 92 |
| II-14 | $C_2H_5$ | $CH(CH_3)_2$ | (amorphous) |
| II-15 | $C_3H_7$ | $CH(CH_3)_2$ | (amorphous) |
| II-16 | $CH(CH_3)_2$ | $CH(CH_3)_2$ | 168 |
| II-17 | $C_2H_5$ | $CH_3$ | 134 |
| II-18 |  | $CH_3$ | 159 |

TABLE 4-continued

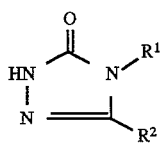

Preparation examples of the compounds of the formula (II)

| Ex. No. | R¹ | R² | m.p. (°C.) |
|---|---|---|---|
| II-19 | OCH₃ | CH₃ | 178 |
| II-20 | OCH₃ | C₂H₅ | 140 |
| II-21 | OCH₃ | C₃H₇ | 127 |
| II-22 | OCH₃ | CH(CH₃)₂ | 130 |
| II-23 | OCH₂C₆H₅ | CH₃ | 106 |
| II-24 | cyclopropyl | C₂H₅ | 150 |
| II-25 | cyclopropyl | C₃H₇ | 130 |
| II-26 | OC₂H₅ | C₃H₇ | 72 |
| II-27 | cyclopropyl | CH(CH₃)₂ | 121 |
| II-28 | CH₃ | C₄H₉ | 50 |
| II-29 | C₂H₅ | C₄H₉ | 76 |
| II-30 | C₃H₇ | C₄H₉ | (amorphous) |
| II-31 | OCH₃ | C₄H₉ | 100 |
| II-32 | cyclopropyl | C₄H₉ | 66 |
| II-33 | CH₃ | cyclopropyl | 68 |
| II-34 | C₂H₅ | cyclopropyl | 130 |
| II-35 | C₃H₇ | cyclopropyl | 68 |
| II-36 | cyclopropyl | cyclopropyl | 154 |
| II-37 | N(CH₃)₂ | CH₃ | 153 |
| II-38 | N(CH₃)₂ | C₂H₅ | 114 |
| II-39 | N(CH₃)₂ | C₃H₇ | 108 |
| II-40 | N(CH₃)₂ | CH(CH₃)₂ | 100 |
| II-41 | CH₃ | N(CH₃)₂ | 80 |
| II-42 | N(CH₃)₂ | cyclopropyl | 134 |
| II-43 | CH(CH₃)₂ | NHCH(CH₃)₂ | 205 |
| II-44 | N(CH₃)₂ | N(CH₃)₂ | 93 |
| II-45 | C₂H₅ | N(CH₃)₂ | 50 |
| II-46 | cyclopentyl | CH₃ | 145 |
| II-47 | cyclohexyl | CH₃ | 163 |
| II-48 | cyclopropyl | H | 102 |
| II-49 | OCH₃ | cyclopropyl | 136–137 |
| II-50 | CH₃ | C₆H₅ | |
| II-51 | NH₂ | H | 192 |
| II-52 | NH₂ | CH₃ | 230 |
| II-53 | NH₂ | CF₃ | 163 |
| II-54 | NHCH₃ | CH(CH₃)₂ | 105 |
| II-55 | NHCH₃ | cyclopropyl | 95 |
| II-56 | NH₂ | C₂H₅ | 170 |
| II-57 | NH₂ | C₃H₇ | 147 |
| II-58 | NHCH₃ | NHCH₃ | 137 |
| II-59 | CH₂C₆H₅ | C₂H₅ | 125 |
| II-60 | NHCH₃ | H | 133 |
| II-61 | NHCH₃ | N(CH₃)₂ | 129 |
| II-62 | NHCH₃ | C₃H₇ | 76 |
| II-63 | NH₂ | 4-Cl-C₆H₄ | 248 |
| II-64 | NH₂ | —CH(CH₃)C₂H₅ | 176 |
| II-65 | NH₂ | cyclopropyl | 183 |
| II-66 | NH₂ | 3-CF₃-C₆H₄ | 210 |
| II-67 | NHCH₃ | C₂H₅ | 101 |
| II-68 | NH₂ | N(C₂H₅)₂ | 196 |
| II-69 | NH₂ | pyrrolidin-1-yl | 233 |
| II-70 | NH₂ | CH(CH₃)₂ | 172 |
| II-71 | NH₂ | C(CH₃)₃ | 261 |
| II-72 | NH₂ | CH₂CH₂OCH₃ | 98 |
| II-73 | NH₂ | C(CH₃)₂C₂H₅ | 213 |
| II-74 | NH₂ | NHC₂H₅ | 220 |
| II-75 | NH₂ | OCH₃ | (amorphous) |
| II-76 | NH₂ | CH₂OCH₃ | 134 |
| II-77 | NH₂ | CH₂OC₂H₅ | 104 |
| II-78 | N(CH₃)₂ | CH₃ | 153 |
| II-79 | —CH₂-C(Cl)₂-cyclopropyl | C₂H₅ | 103 |
| II-80 | —CH₂CH(CH₃)₂ | C₂H₅ | 105 |
| II-81 | C₆H₅ | H | 183 |
| II-82 | N(CH₃)₂ | CH(CH₃)₂ | (amorphous) |
| II-83 | NHCH₃ | CH₃ | 114 |
| II-84 | NH₂ | CH₂C₆H₅ | 168 |

TABLE 4-continued $$\text{(II)} \quad \underset{HN}{\overset{O}{\|}}\!\!\!-\!\!\!\underset{\underset{N}{|}}{C}\!\!\!-\!\!\!N\!\!\!<\!\!\overset{R^1}{\underset{=\!C\!-\!R^2}{}}$$

Preparation examples of the compounds of the formula (II)

| Ex. No. | R¹ | R² | m.p. (°C.) |
|---|---|---|---|
| II-85 | NH₂ | N(CH₃)₂ | 207 |
| II-86 | NH₂ | C₆H₅ | 230 |
| II-87 | NH₂ | —⬡ (cyclohexenyl) | 223 |
| II-88 | NH₂ | NHCH(CH₃)₂ | 152 |
| II-89 | NHCH₃ | NHCH(CH₃)₂ | 120 |
| II-90 | —⬡H (cyclohexyl) | NH—⬡H (cyclohexylamino) | 254 |
| II-91 | △ (cyclopropyl) | N(CH₃)₂ | |
| II-92 | CH₂C₆H₅ | H | 111 |
| II-93 | C₃H₇ | H | 48 |
| II-94 | C₆H₅ | C₂H₅ | 124 |
| II-95 | C(CH₃)₃ | C₂H₅ | 158 |
| II-96 | CH₃ | H | 157 |
| II-97 | □ (cyclobutyl) | C₂H₅ | 108 |
| II-98 | ⬠ (cyclopentyl) | C₂H₅ | 132 |
| II-99 | —CH₂CH=CH₂ | CH₃ | 108 |
| II-100 | C₆H₅ | CH₃ | 150 |
| II-101 | ◇ (cyclobutyl) | CH₃ | 116 |
| II-102 | —⬡H (cyclohexyl) | C₂H₅ | 146 |
| II-103 | C₂H₅ | H | 68 |
| II-104 | CH(CH₃)₂ | H | 105 |
| II-105 | ⬠ (cyclopentyl) | H | 79 |
| II-106 | —⬡H (cyclohexyl) | H | 162 |
| II-107 | C(CH₃)₃ | H | 194 |
| II-108 | —CH₂—CH(Br)—CH₂Br | CH₃ | 111 |
| II-109 | CH₃ | —CH₂OCH₃ | 104 |
| II-110 | CH₃ | —CH₂OC₂H₅ | 102 |
| II-111 | △ | —CH₂OCH₃ | 102 |
| II-112 | △ | —CH₂OC₂H₅ | 119 |
| II-113 | △ | —N(CH₃)₂ | 130 |
| II-114 | NH₂ | —N(CH₃)(C₂H₅) | 186 |
| II-115 | NH₂ | —N(CH₃)(C₃H₇-n) | 165 |
| II-116 | NH₂ | —N(C₂H₅)(C₃H₇-n) | 186 |
| II-117 | NH₂ | —N(morpholino) | 267 |
| II-118 | CH₃ | —OCH₃ | 144 |

The compound of Example (II-118) disclosed Table 4 (above) can be prepared as follows:

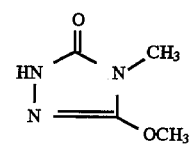

(II-118)

50.2 g (0.33 mol) of hydrazino-formic acid phenyl ester (=1-phenoxycarbonyl-hydrazine) and 36.6 g (0.33 mol; 90% purity) of O,O,N-trimethyl-iminocarbonate are mixed at 40° C. with 100 ml of 1,2-dichlorobenzene, and this mixture is then stirred for two hours at 60° C. Thereafter the mixture is heated further up to 120° C., while methanol (formed during the reaction) is being distilled off. Then the reaction mixture is cooled and heated again in vacuo (0.01 mbar) to a temperature of 120° C. in order to remove any remaining volatile compounds (methanol, phenol and 1,2-dichlorobenzene) from the reaction mixture. An a temperature above 120° C. the reaction product is distilled roughly and then crystallized from toluene.

This gives 7.5 g (18% of theory) of 5-methoxy-4-methyl-2,4-dihydro-3H-1,2,4-triazol-one as colorless crystals of melting point 144° C.

EXAMPLE (II-119)

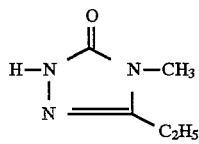

57 g (1 mol) of methyl isocyanate are added dropwise at 20° C. to 30° C. to a stirred mixture of 50 g (1 mol) of hydrazine hydrate and 200 ml of water; the reaction mixture is stirred for 2 hours at 200° C. to 30° C., and the solvent is then carefully distilled off under a water-pump vacuum.

The resulting methylaminocarbonylhydrazine ($H_2N$—NH—CO—NHCH$_3$)—82.5 g (0.93 mol)—is taken up in 800 ml of methylene chloride, and 114 g (0.88 mol) of propionic anhydride are added dropwise at 20° C. to 30° C. to the stirred mixture. The reaction mixture is refluxed for 30 minutes and then stirred at 20° C. for 15 hours. The product which is obtained in the form of crystals is isolated by filtering off with suction.

The resulting N-methylaminocerbonyl-N'-propionyl-hydrazine ($H_5C_2$—CO—NH—NH—CO—NHCH$_3$)—114 g (0.79 mol)—is added to a solution of 31.4 (0.79 mol) of sodium hydroxide in 2.4 l of water and the reaction mixture is stirred at 90° C. for 60 minutes. The mixture is then evaporated, the residue is stirred with 300 ml of ethanol/ethyl acetate, and the mixture is filtered. The filtrate is concentrated and stirred with diethyl ether, and the product which is obtained in the form of crystals in this process is isolated by filtering off with suction.

67.4 g (67% of theory) of 5-ethyl-4-methyl-2,4-dihydro-3H-1,2,4-triazolo-3-one of melting point 86° C. are obtained.

STARTING SUBSTANCES OF THE FORMULA (III)

EXAMPLE (III-1)

900 g (5.1 mol) of 2-trifluoromethoxy-toluene (2-methyl-trifluoroanisole) are heated at 100° C., and 180 g (2.54 mol) of chlorine are passed in at this temperature and with UV irradiation. Nitrogen is then blown in, the reaction mixture is subjected to fractional distillation under reduced pressure.

As the main fraction, 425 g (40% of theory) of 2-trifluoromethoxy-benzyl chloride (2-chloromethyl-trifluoroanisole) of boiling point 110° C./100 mbar and of refractive index $n_D^{20}=1.5450$ are obtained.

21.0 g (0.1 mol) of 2-trifluoromethoxy-benzyl chloride and a saturated solution of 13.9 g (0.11 mol) of sodium sulphite in water are refluxed for 5 hours with vigorous stirring. After cooling, the precipitated white solids are filtered off with suction and rinsed with a small amount of ice-cold water.

After drying over phosphorus pentoxide, 26.4 g (95% of theory) of sodium 2-trifluoromethoxy-benzyl-sulphonate of melting point 115° C. are obtained.

23.7 g (0.085 mol) of sodium 2-trifluoromethoxy-benzylsulphonate are mixed with 35.5 g (0.17 mol) of phosphorus pentachloride, and the mixture is swirled for approx. 2 hours on a rotary evaporator at 80° C.–90° C. bath temperature. The mixture is cooled, and the phosphorus oxychloride which has formed is removed in vacuo. The residue is suspended in methylene chloride, and the mixture is poured into ice water. The organic phase is separated off, washed to neutrality, dried and concentrated.

19.0 g (81.4% of theory) of 2-trifluoromethoxy-benzylsulphonyl chloride are obtained as a crude product which is sufficiently pure for the subsequent reaction to give the sulphonamide. For purification, the crude product can be taken up in methylene chloride and purified over silica gel $n_D^{22.5}=1.4854$.

205.9 g (0.75 mol) of 2-trifluoromethoxy-benzylsulphonyl chloride are introduced at 30° C.–400° C. into 1.5 l of a saturated aqueous ammonia solution, and the mixture is subsequently stirred at 50° C.–60° C. for 3 hours. After cooling, the precipitated solids are filtered off with suction, washed to neutrality with water and dried.

136.5 g (71% of theory) of 2-trifluoromethoxy-benzylsulphonamide of melting point 127° C. are obtained.

A mixture of 8.9 g (0.035 mol) of 2-trifluoromethoxybenzylsulphonamide, 3.5 g (0.035 mol) of n-butyl isocyanate, 0.2 g of diaza-bicyclo-[2.2.2]-octane (DABCO) and 150 ml of anhydrous xylene is heated at reflux temperature and a weak stream of phosgene is passed in for two hours. The mixture is subsequently stirred under reflux conditions for 30 minutes, then cooled, filtered and evaporated. The residue is taken up in methylene chloride and refiltered. The filtrate contains 2-trifluoromethoxy-benzylsulphonyl isocyanate as a crude product in a mixture with DABCO and is used further as such for the subsequent reaction since partial decomposition occurs on high-vacuum distillation.

Examples of hydrazine derivatives of the formula (IX) which can be obtained analogously to Example (II-1), step 1, are listed in Table 5 below.

TABLE 5

$$H-N-CO-NH-R^1 \quad (IX)$$
$$H-N-CO-R^2$$

Examples of the hydrazine derivatives of the formula (IX)

| Ex. No. | R$^1$ | R$^2$ | m.p. (°C.) |
|---|---|---|---|
| IX-2 | OCH$_3$ | C$_2$H$_5$ | 120 |
| IX-3 | OCH$_3$ | C$_3$H$_7$ | 125 |
| IX-4 | OCH$_3$ | CH(CH$_3$)$_2$ | 127 |
| IX-5 | OCH$_2$C$_6$H$_5$ | CH$_3$ | 100 |
| IX-6 | △ | C$_2$H$_5$ | 174 |
| IX-7 | △ | C$_3$H$_7$ | 180 |
| IX-8 | OC$_2$H$_5$ | C$_3$H$_7$ | 119 |
| IX-9 | △ | CH(CH$_3$)$_2$ | 150 |
| IX-10 | OCH$_3$ | C$_4$H$_9$ | 134 |
| IX-11 | △ | C$_4$H$_9$ | 159 |
| IX-12 | △ | △ | 188 |

TABLE 5-continued $$H-N-CO-NH-R^1 \quad (IX)$$
$$|$$
$$H-N-CO-R^2$$

Examples of the hydrazine derivatives of the formula (IX)

| Ex. No. | R¹ | R² | m.p. (°C.) |
|---|---|---|---|
| IX-13 | OCH₃ | △ | 140 |
| IX-14 | CH₂—CH=CH₂ | C₃H₇ | 134 |
| IX-15 | △ | —CH₂OC₂H₅ | 97 |

STARTING SUBSTANCES OF THE FORMULA (IV)

EXAMPLE (IV-1)

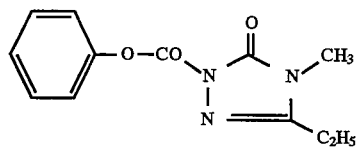

6.4 g (0.05 mol) of 5-ethyl-4-methyl-2,4-dihydro-3H-1,2,4-triazol-3-one are dissolved in 80 ml of tetrahydrofuran, and 1.8 g (0.06 mol) of sodium hydride (80% of substance) are added under nitrogen. After the mixture has been stirred for one hour at 20° C., 7.9 g (0.05 mol) of phenyl chloroformate are added dropwise, and the reaction mixture is stirred at 20° C. for a further 20 hours. After the mixture has been concentrated, the residue is taken up in methylene chloride, and the mixture is washed with water, dried with sodium sulphate and filtered. The filtrate is concentrated, the residue is triturated with diethyl ether, and the product which has been obtained in crystalline form is isolated by filtration with suction.

This gives 4.5 g (36% of theory) of 5-ethyl-4-methyl-2-phenoxycarbonyl-2,4-dihydro-3H-1,2,4-triazol-3-one of melting point 141° C.

For example the compounds of the formula (IV) listed in Table 6 below can also be prepared analogously to Example (IV-1).

TABLE 6

$$\begin{array}{c}O\\\|\\Z-CO\diagdown_N\diagup^{\!\!\!\!C}\diagdown_{N}\diagup^{R^1}\\|\\N=\!\!\!=\!\!\!=_{R^2}\end{array} \quad (IV)$$

Examples of the compounds of the formula (IV)

| Ex. No. | R¹ | R² | Z | m.p. (°C.) |
|---|---|---|---|---|
| IV-2 | C₃H₇ | C₃H₇ | C₆H₅ | 88 |
| IV-3 | OCH₃ | C₃H₇ | C₆H₅ | 82 |
| IV-4 | CH₃ | C₃H₇ | C₆H₅ | 84 |
| IV-5 | NH₂ | C₃H₇ | C₆H₅ | 133 |

TABLE 6-continued $$\begin{array}{c}O\\\|\\Z-CO\diagdown_N\diagup^{\!\!\!\!C}\diagdown_{N}\diagup^{R^1}\\|\\N=\!\!\!=\!\!\!=_{R^2}\end{array} \quad (IV)$$

Examples of the compounds of the formula (IV)

| Ex. No. | R¹ | R² | Z | m.p. (°C.) |
|---|---|---|---|---|
| IV-6 | NH₂ | CH₃ | C₆H₅ | 82 |
| IV-7 | △ | C₂H₅ | C₆H₅ | 152 |
| IV-8 | OC₂H₅ | C₂H₅ | C₆H₅ | |
| IV-9 | OCH₂CH=CH₂ | CH₃ | C₆H₅ | |
| IV-10 | ⬠ | C₄H₉ | C₆H₅ | |
| IV-11 | CH₃ | △ | C₆H₅ | |
| IV-12 | NHCH₃ | C₂H₅ | C₆H₅ | |
| IV-13 | CH₃ | CH₂C₆H₅ | C₆H₅ | |
| IV-14 | CH₃ | NHCH(CH₃)₂ | C₆H₅ | |
| IV-15 | N(CH₃)₂ | N(CH₃)₂ | C₆H₅ | |
| IV-16 | △ | △ | C₆H₅ | |
| IV-17 | OC₂H₅ | △ | C₆H₅ | |
| IV-18 | OC₃H₇ | C₂H₅ | C₆H₅ | |
| IV-19 | C₂H₅ | C₄H₉ | C₆H₅ | |
| IV-20 | CH(CH₃)₂ | CH(CH₃)₂ | C₆H₅ | |
| IV-21 | OCH₃ | C₂H₅ | C₆H₅ | 89 |
| IV-22 | △ | C₃H₇-n | C₆H₅ | 104 |

Use Examples:

In the following use examples, the known herbicide isocarbamide, of formula (A) below, is used as comparison substance:

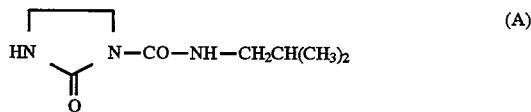
(A)

The formulae of the compounds according to the invention used in the Use Examples are listed individually below in conjunction with the number of the Preparation Examples:

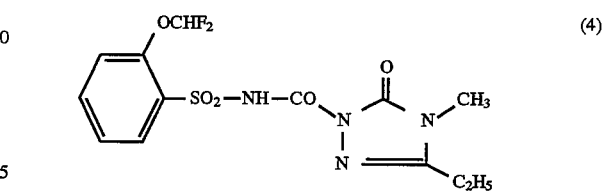
(4)

113
-continued
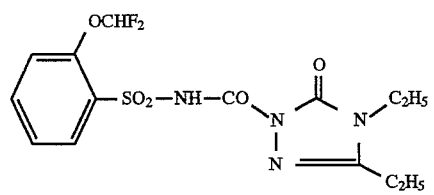 (5)
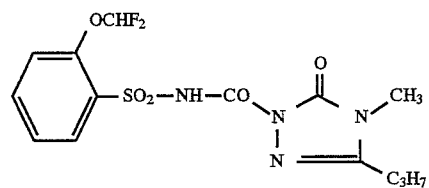 (6)
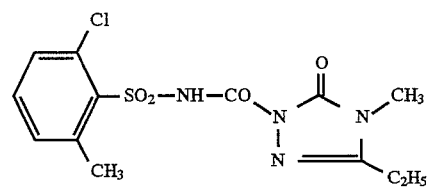 (2)
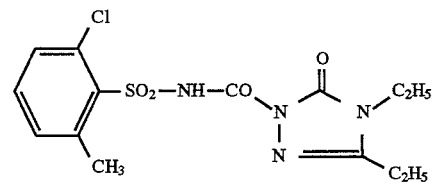 (7)
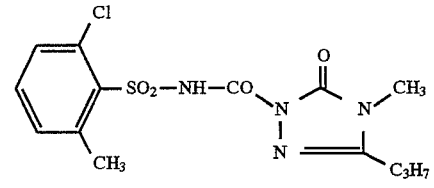 (8)
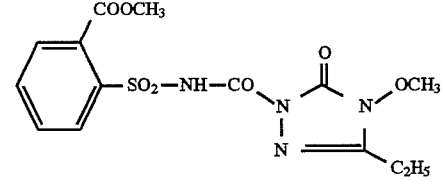 (12)
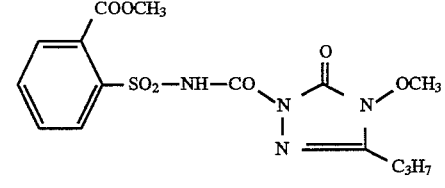 (13)
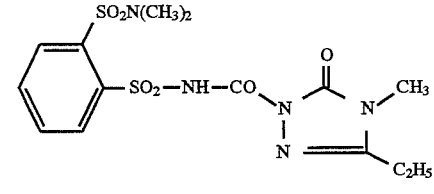 (14)
114
-continued
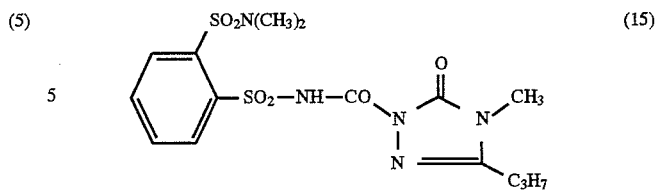 (15)
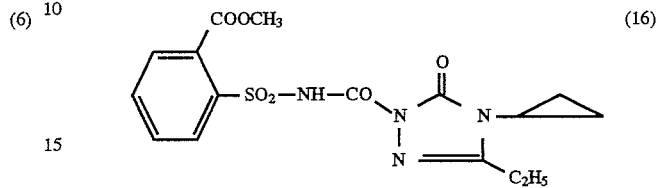 (16)
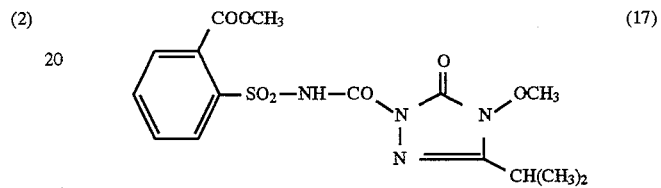 (17)
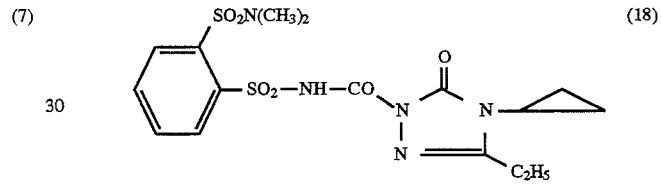 (18)
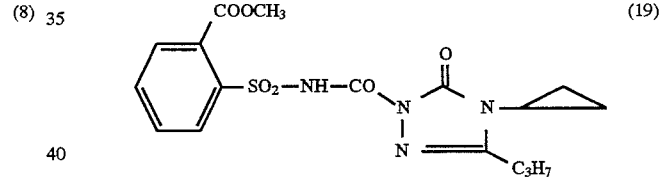 (19)
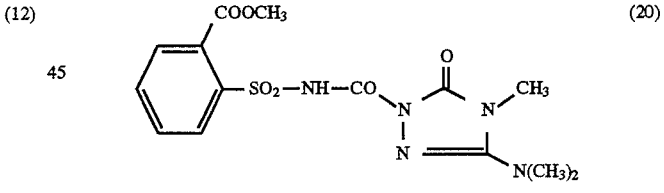 (20)
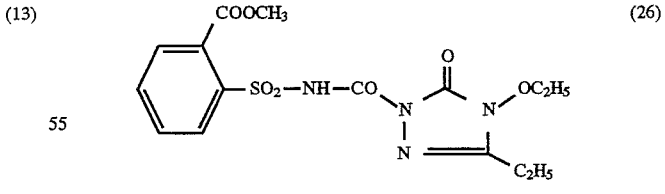 (26)
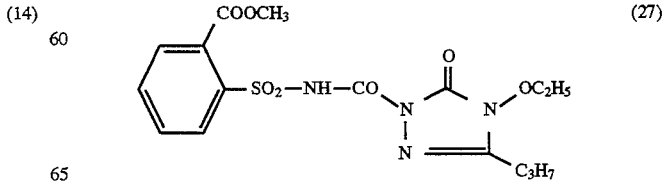 (27)

-continued
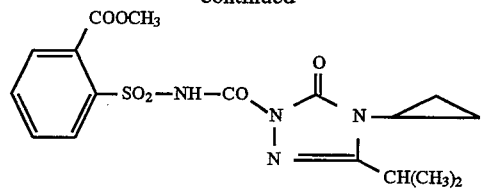 (28)
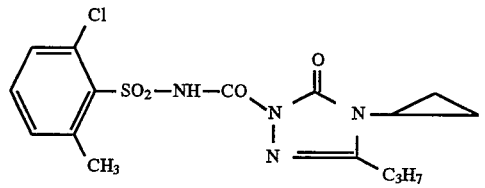 (29)
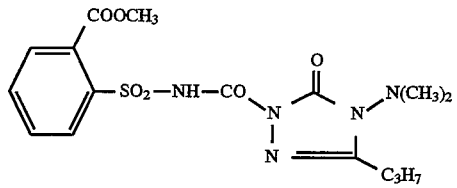 (30)
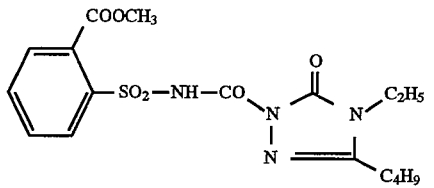 (32)
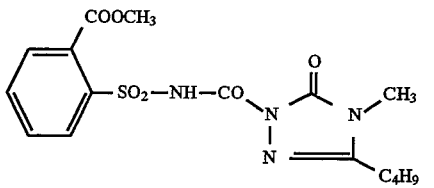 (33)
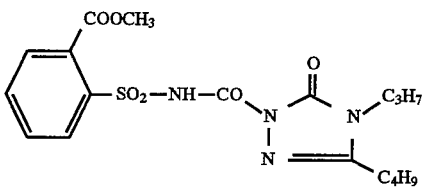 (34)
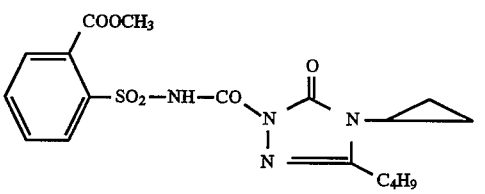 (35)
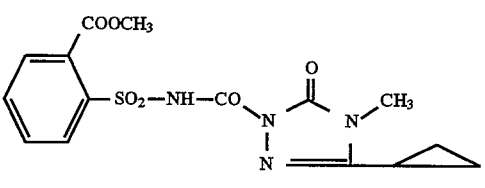 (37)
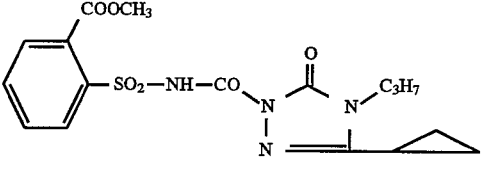 (39)
-continued
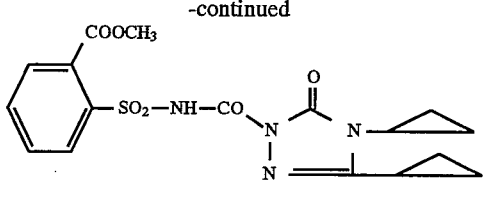 (40)
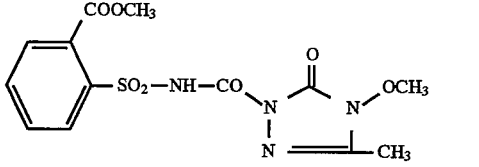 (9)
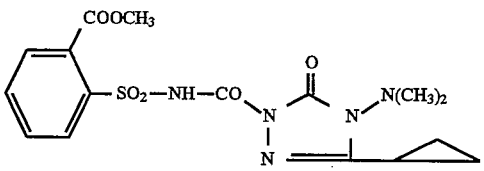 (31)
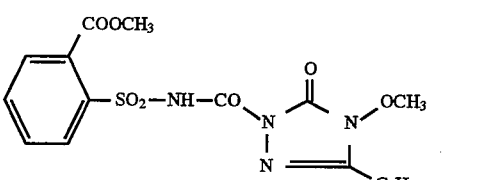 (36)
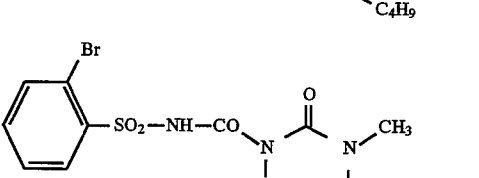 (126)
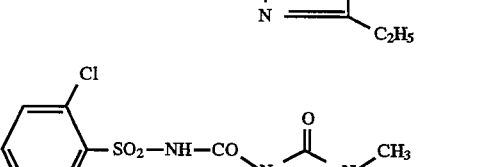 (128)
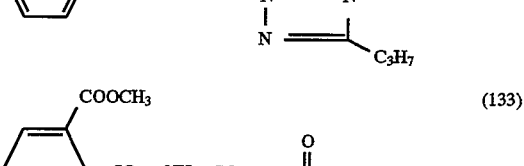 (133)
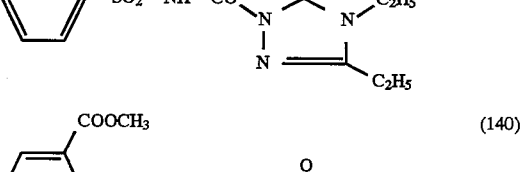 (140)
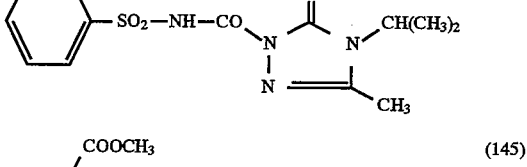 (145)

-continued

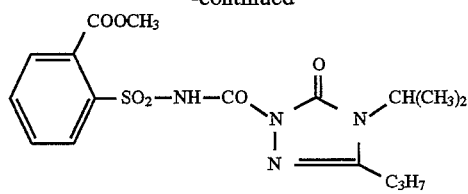
(147)

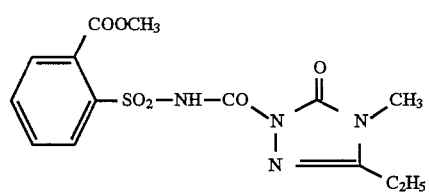
(152)

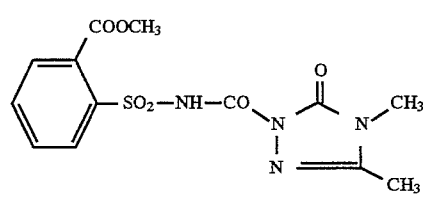
(153)

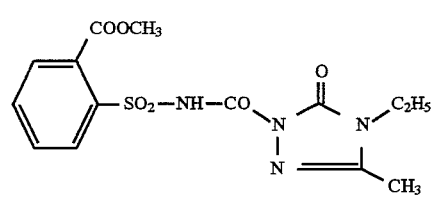
(154)

EXAMPLE A

Pre-emergence test

Solvent: 5 parts by weight of acetone

Emulsifier: 1 part by weight of alkylaryl polyglycol ether

To prepare a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil and, after 24 hours, watered with the preparation of active compound. It is expedient here to keep constant the amount of water per unit area. The concentration of active compound in the preparation is of no importance, only the amount of active compound applied per unit area being decisive. After three weeks, the degree of damage of the plants is rated in % damage in comparison with the development of the untreated control. The figures denote:

0%=no action (like untreated control)

100%=total destruction

In this test a clearly superior activity compared with the prior art is shown, for example, by the compounds of Preparation Examples 2, 6, 8, 12, 13, 16, 17, 18, 19, 20, 26, 27, 28, 29, 34, 37, 39, 40 and 133.

EXAMPLE B

Post-emergence test

Solvent: 5 parts by weight of acetone

Emulsifier: 1 part by weight of alkylaryl polyglycol ether

To prepare a suitable preparation of active compound, 1 part by weight of active compound is mixed with the stated amount of solvent, the stated amount of emulsifier is added, and the concentrate is diluted with water to the desired concentration.

Test plants having a height of 5–15 cm are sprayed with the preparation of active compound in such a way that the specifically desired amounts of active compound per unit area are applied, The concentration of the spray liquor is chosen in such a way that the specifically desired amounts of active substance are applied in 1000 l of water/ha. After three weeks, the degree of damage of the plants is rated in % damage in comparison with the development of the untreated control. The figures denote:

0%=no action (like untreated control)

100%=total destruction

In this test a clearly superior activity compared with the prior art is shown, for example, by the compounds of Preparation Examples 2, 4, 5, 6, 7, 8, 12, 13, 14, 15, 16, 17, 18, 19, 20, 26, 27, 28, 29, 30, 32, 33, 34, 35, 37, 39, 40, 126,128 and 133.

EXAMPLE C

Pyricularia test (rice)/protective

Solvent: 12,5 parts by weight of acetone

Emulsifier: 0,3 parts by weight of alkylarylpolyglycol ether

To produce a suitable preparation of active compound, 1 part by weight of active compound is mixed with the stated amount of solvent, and %he concentrate is diluted with water and the stated amount of emulsifier to the desired concentration.

To test for protective activity, young rice plants are sprayed with the preparation of active compound until dripping wet. After the spray coating has dried off, the plants are inoculated with an aqueous spore suspension of *Pyricularia orycae*. The plants are then placed in a greenhouse at 100% relative atmospheric humidity and 25° C.

Evaluation of the disease infestation is carried out 4 days after the inoculation.

In this test, a very good activity is shown, for example, by the compounds according to the following preparation examples:

9, 12, 13, 20, 30, 31, 32, 33, 34, 35, 36, 37, 140, 145, 147, 152, 153, 154.

EXAMPLE D

Pyricularia Test (rice)/systemic

Solvent : 12,5 parts by weight of acetone

Emulsifier: 0,3 parts by weight of alkylaryl-polyglycol ether

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° and a relative atmospheric humidity of 100% until they are evaluated.

Evaluation of the disease infestation is carried out 4 days after the inoculation.

In this test, an excellent activity is shown, for example, by the compounds according to the following preparation examples:

9, 12, 13, 20, 30, 31, 32, 33, 34, 35, 36, 37, 140, 145, 147, 152, 153, 154.

It will be appreciated that the instant specification and claims are set forth by way of illustration and not limitation, and that various modifications and changes may be made without departing from the spirit and scope of the present invention.

We claim:

1. A triazolinone of the formula

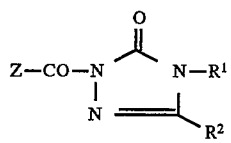

in which

Z is chlorine, $C_1$–$C_4$-alkoxy, benzyloxy or phenoxy, a) $R^1$ is di-($C_1$–$C_4$-alkyl)-amino, and $R^2$ is hydrogen or $C_1$–$C_6$-alkyl which is optionally substituted by fluorine, chlorine, bromine, cyano, $C_3$–$C_6$-cycloalkyl, $C_1$–$C_4$-alkoxy or $C_1$–$C_4$-alkoxycarbonyl, or is $C_3$–$C_6$-cycloalkyl which is optionally substituted by fluorine, chlorine, bromine and/or $C_1$–$C_4$-alkyl, or is cyclohexenyl, or is phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxycarbonyl, or is phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl, and/or $C_1$–$C_4$-alkoxycarbonyl, or is $C_1$–$C_6$-alkoxy which is optionally substituted by fluorine, chlorine, cyano, $C_1$–$C_4$-alkoxy or $C_1$–$C_4$-alkoxy-carbonyl;

or in which b) $R^1$ is $C_1$–$C_4$-alkoxy (which is optionally substituted by fluorine, chlorine, bromine, cyano, phenyl, $C_1$–$C_4$-alkoxy or $C_1$–$C_4$-alkoxycarbonyl) or is $C_3$–$C_4$-alkenyloxy, and $R^2$ is hydrogen or is $C_1$–$C_4$-alkyl which is optionally substituted by fluorine, chlorine, bromine, cyano, $C_1$–$C_4$-alkoxy, $C_1$–$C_4$-alkyl-carbonyl, or $C_1$–$C_4$-alkoxycarbonyl, or is $C_3$–$C_6$-cycloalkyl which is optionally substituted by fluorine, chlorine, bromine, and/or $C_1$–$C_4$-alkyl, or is phenyl-$C_1$–$C_3$-alkyl, which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxycarbonyl, or is phenyl which is optionally substituted by fluorine, chlorine, bromine, cyano, nitro, $C_1$–$C_4$-alkyl, trifluoromethyl, methyl, $C_1$–$C_4$alkoxy, fluorine and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl, and/or $C_1$–$C_4$-alkoxycarbonyl;

or in which

| $R^1$ is | and | $R^2$ is |
|---|---|---|
| c)  | | $C_3H_7$, |
|  | | $CH(CH_3)_2$, |
|  | | $C_4H_9$, |
| $CH_3$ | | , |
| $C_2H_5$ | | , |
| $C_3H_7$ | | , |
|  | | , |
| 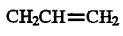 | | H, |
| 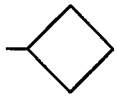 | | $C_2H_5$, |
| $CH_2CH=CH_2$ | | $CH_3$, |
|  | | $CH_3$, |
| $CH_3$ | | $-CH_2OCH_3$, |
|  | | $-CH_2OCH_3$, |
|  | | $-CH_2OC_2H_5$, |
|  | | $-N(CH_3)_2$. |

2. A triazolinone according to claim 1, in which Z is phenoxy.

3. A triazolinone according to claim 1, in which a) $R^1$ is di-($C_1$–$C_4$-alkyl)-amino, and $R^2$ is hydrogen or $C_1$–$C_6$-alkyl which is optionally substituted by fluorine, chlorine, bromine, cyano, $C_3$–$C_6$-cycloalkyl, $C_1$–$C_4$-alkoxy or $C_1$–$C_4$-alkoxycarbonyl, or is $C_3$–$C_6$-cycloalkyl which is optionally substituted by fluorine, chlorine, bromine and/or $CC_1$–$C_4$-alkyl, or is cyclohexenyl, or is phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxycarbonyl, or is phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl, and/or $C_1$–$C_4$-alkoxycarbonyl, or is $C_1$–$C_6$-alkoxy which is optionally substituted by fluorine, chlorine, cyano, $C_1$–$C_4$-alkoxy or $C_1$–$C_4$-alkoxy-carbonyl.

4. A triazolinone according to claim 1, in which b) $R^1$ is $C_1$–$C_6$-alkoxy (which is optionally substituted by fluorine, chlorine, bromine, cyano, phenyl, $C_1$–$C_4$-alkoxy or $C_1$–$C_4$-alkoxycarbonyl) or is $C_3$–$C_4$-alkenyloxy, and $R^2$ is hydrogen or is $C_1$–$C_6$-alkyl which is optionally substituted by fluorine, chlorine, bromine, cyano, $C_1$–$C_4$-alkoxy, $C_1$–$C_4$-alkyl-carbonyl, or $C_1$–$C_4$-alkoxycarbonyl, or is $C_3$–$C_6$-cycloalkyl which is optionally substituted by fluorine, chlorine, bromine, and/or $C_1$–$C_4$alkyl, or is phenyl-$C_1$–$C_3$-alkyl, which is optionally substituted by fluorine, chlorine, bromine, cyano, nitro, $C_1$–$C_4$alkyl, trifluoromethyl, $C_1$–$C_4$-alkoxy and/or $C_1$–$C_4$-alkoxycarbonyl, or is phenyl which is optionally substituted by fluorine, chlorine, bromine, cyano, nitro, $C_1$–$C_4$-alkyl, trifluoromethyl, methyl, $C_1$–$C_4$-alkoxy, fluorine and/or chlorine-substituted $C_1$–$C_3$-alkoxy, $C_1$–$C_4$-alkylthio, fluorine and/or chlorine-substituted $C_1$–$C_3$-alkylthio, $C_1$–$C_4$-alkylsulphinyl, $C_1$–$C_4$-alkylsulphonyl, and/or $C_1$–$C_4$-alkoxycarbonyl.

5. A triazolinone according to claim 1, in which

| $R^1$ is | and | $R^2$ is |
|---|---|---|
| c) △ | | $C_3H_7$, |
| △ | | $CH(CH_3)_2$, |
| △ | | $C_4H_9$, |
| $CH_3$ | | △, |
| $C_2H_5$ | | △, |
| $C_3H_7$ | | △, |
| △ | | △, |
| △ | | H, |
| ▢ | | $C_2H_5$, |
| $CH_2CH=CH_2$ | | $CH_3$, |
| ◇ | | $CH_3$, |
| $CH_3$ | | —$CH_2OCH_3$, |
|  | | —$CH_2OCH_3$, |

-continued

| | | |
|---|---|---|
|  | | —$CH_2OC_2H_5$, |
|  | | —$N(CH_3)_2$. |

6. A triazolinone according to claim 1, in which $R^1$ is $N(CH_3)_2$ and $R^2$ is H.

7. A triazolinone according to claim 1, in which $R^1$ is $N(CH_3)_2$ and $R^2$ is $CH_3$.

8. A triazolinone according to claim 1, in which $R^1$ is $N(CH_3)_2$ and $R^2$ is $C_2H_5$.

9. A triazolinone according to claim 1, in which $R^1$ is $N(CH_3)_2$ and $R^2$ is $C_3H_7$.

10. A triazolinone according to claim 1, in which $R^1$ is $N(CH_3)_2$ and $R^2$ is $CH(CH_3)_2$.

11. A triazolinone according to claim 1, in which $R^1$ is $N(CH_3)_2$ and $R^2$ is

12. A triazolinone according to claim 1, in which $R^1$ is $OCH_3$ and $R^2$ is $CH_3$.

13. A triazolinone according to claim 1, in which $R^1$ is $OCH_3$ and $R^2$ is $C_2H_5$.

14. A triazolinone according to claim 1, in which $R^1$ is $OCH_3$ and $R^2$ is $C_3H_7$.

15. A triazolinone according to claim 1, in which $R^1$ is $OC_2H_5$ and $R^2$ is $C_2H_5$.

16. A triazolinone according to claim 1, in which $R^1$ is $OCH_3$ and $R^2$ is $CH(CH_3)_2$.

17. A triazolinone according to claim 1, in which $R^1$ is $OCH_2C_6H_5$ and $R^2$ is $CH_3$.

18. A triazolinone according to claim 1, in which $R^1$ is $OC_2H_5$ and $R^2$ is $C_3H_7$.

19. A triazolinone according to claim 1, in which $R^1$ is $OCH_3$ and $R^2$ is $C_4H_9$.

20. A triazolinone according to claim 1, in which $R^1$ is $OCH_3$ and $R^2$ is

* * * * *

UNITED STATES PATENT AND TRADEMARK OFFICE
CERTIFICATE OF CORRECTION

PATENT NO. : 5,625,074
DATED : April 29, 1997
INVENTOR(S) : Daum, et al.

It is certified that error appears in the above-indentified patent and that said Letters Patent is hereby corrected as shown below:

Col. 120, line 48    Delete " $CC_1-C_4$-alkyl " and substitute -- $C_1-C_4$-alkyl --

Signed and Sealed this

Seventeenth Day of November, 1998

Attest:

BRUCE LEHMAN

Attesting Officer    Commissioner of Patents and Trademarks